United States Patent
Beaucage et al.

(10) Patent No.: US 7,612,197 B2
(45) Date of Patent: Nov. 3, 2009

(54) THERMOLABILE HYDROXYL PROTECTING GROUPS AND METHODS OF USE

(75) Inventors: Serge L Beaucage, Silver Spring, MD (US); Marcin K Chmielewski, Poznan (PL)

(73) Assignee: The United States of America as repesented by the Secretary of the Department of Health and Human Services, Washington, DC (US)

(*) Notice: Subject to any disclaimer, the term of this patent is extended or adjusted under 35 U.S.C. 154(b) by 379 days.

(21) Appl. No.: 10/556,219

(22) PCT Filed: May 7, 2004

(86) PCT No.: PCT/US2004/014185

§ 371 (c)(1),
(2), (4) Date: Nov. 9, 2005

(87) PCT Pub. No.: WO2004/101582

PCT Pub. Date: Nov. 25, 2004

(65) Prior Publication Data

US 2006/0281911 A1  Dec. 14, 2006

Related U.S. Application Data

(60) Provisional application No. 60/469,312, filed on May 9, 2003.

(51) Int. Cl.
*C07H 21/00* (2006.01)
(52) U.S. Cl. .................. 536/25.3; 536/22.1; 536/25.31
(58) Field of Classification Search ........................ None
See application file for complete search history.

(56) References Cited

U.S. PATENT DOCUMENTS

| | | |
|---|---|---|
| 4,415,732 A | 11/1983 | Caruthers et al. |
| 4,668,777 A | 5/1987 | Caruthers et al. |
| 4,845,205 A | 7/1989 | Huynh Dinh et al. |
| 4,973,679 A | 11/1990 | Caruthers et al. |
| 5,525,719 A | 6/1996 | Srivastava et al. |
| 5,550,098 A | 8/1996 | Aso et al. |
| 5,705,621 A | 1/1998 | Ravikumar |
| 5,763,599 A | 6/1998 | Pfleiderer et al. |
| 5,889,165 A | 3/1999 | Fodor et al. |

FOREIGN PATENT DOCUMENTS

| WO | WO 00/56749 A1 | 9/2000 |
|---|---|---|
| WO | WO 03/048179 A2 | 6/2003 |

OTHER PUBLICATIONS

Fife et al. JACS (1981), vol. 103, pp. 4194-4199.*
Chmielewski et al., *J. Org. Chem.*, 68, 10003-10012 (2003).
Gray et al., *J. Am. Chem. Soc.*, 81, 4351-4355 (1959).
Weiner et al., *J. Org. Chem.*, 14, 868-872 (1949).

* cited by examiner

*Primary Examiner*—Patrick T Lewis
(74) *Attorney, Agent, or Firm*—Leydig, Voit & Mayer, Ltd.

(57) ABSTRACT

Provided is a hydroxyl-protected alcohol comprising a thermolabile hydroxyl-protecting group comprising a 2-pyridyl substituent and a precursor of the thermolabile hydroxyl-protected alcohol. An exemplary thermolabile hydroxyl-protected alcohol is represented by the formula Pg-O—R, wherein Pg is a protecting group of the formula: (Formula) wherein: A is a 2-pyridyl; Z is $CH_2$ or $NR^1$; $R^1$, $R^2$, $R^{2'}$, $R^3$ and $R^{3'}$ are the same or different and each can be, e.g., H, alkyl, or alkyl comprising an aryl substituent; W is CO, CS, or SO; and R is the organic residue of the hydroxyl-protected alcohol. Also provided is a method of producing an alcohol, which method comprises heating the hydroxyl-protected alcohol, which optionally may be obtained from a precursor, at a temperature effective to cleave the hydroxyl-protecting group. The method can be used to produce oligonucleotides.

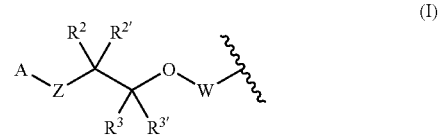

(I)

27 Claims, 7 Drawing Sheets

THERMOLABILE HYDROXYL PROTECTING GROUPS AND METHODS OF USE

FIELD OF THE INVENTION

This invention pertains to thermolabile hydroxyl protecting groups and their use in organic synthesis.

BACKGROUND OF THE INVENTION

Protecting groups and associated deprotection methods are widely used in organic synthesis. See, e.g., Greene et al., Protective Groups in Organic Synthesis, 3rd Ed., John Wiley & Sons, Inc., New York, N.Y. (1999). Protecting groups are often used to prevent a particular functional group or part of a molecule (e.g., an amine, a carboxylic acid, a hydroxyl, a heterocycle, etc.) from reacting under certain reaction conditions (e.g., a chemical reaction in which an unprotected part of the same molecule undergoes a synthetic transformation). Hydroxyl-protecting groups are among the most commonly used protecting groups and are of great importance in organic synthesis. Hydroxyl-protecting groups are particularly useful in the synthesis of oligonucleotides, which are the subject of extensive research and development efforts in view of their significant potential therapeutic applications.

The therapeutic application of oligonucleotides is based on the selective formation of hybrids between antisense oligonucleotides and complementary nucleic acids, such as messenger RNAs (mRNAs). Such hybrids inhibit gene expression by preventing the translation of mRNAs into proteins. Nuclease-resistant oligonucleotides, such as thioated oligonucleotides, are highly desirable in this regard. The discovery and development of improved methods for synthesizing nuclease-resistant oligonucleotides continue to be important goals in medicinal chemistry research.

The method most commonly used for the synthesis of thioated oligonucleotides is the phosphoramidite method with stepwise sulfurization (see, e.g., U.S. Pat. Nos. 4,415,732; 4,668,777; 4,973,679; 4,845,205; and 5,525,719). Alternatively, oligonucleotides can be synthesized using an N-acylphosphoramidite method with stepwise sulfurization (see International Patent Application Publication No. WO 00/56749). In such methods, each coupling step typically is performed with a hydroxyl-protected nucleoside phosphoramidite or N-acylphosphoramidite (e.g., a nucleoside or oligonucleotide phosphoramidite or N-acylphosphoramidite bearing a 5'- or a 3'-hydroxyl protecting group). After each nucleotide addition cycle, the terminal hydroxyl-protecting group is removed so that the next coupling step can be carried out in succession. Acid-labile hydroxyl-protecting groups in oligonucleotide synthesis are known. Examples of acid-labile hydroxyl protecting groups are described in U.S. Pat. Nos. 4,415,732; 4,668,777; and 5,705,621. Such hydroxyl-protecting groups require acidic conditions for deprotection, which is particularly disadvantageous when the oligonucleotide is acid-labile or contains one or more acid-labile functional groups. Photolabile hydroxyl-protecting groups have been described, e.g., in U.S. Pat. Nos. 5,889,165 and 5,763,599. However, photolabile hydroxyl-protecting groups require photochemical conditions for their removal, which is particularly disadvantageous when the oligonucleotide is photosensitive or contains one or more photosensitive functional groups. Accordingly, the range of structural oligonucleotide analogs that can be prepared using conventional hydroxyl protection technology is often limited to those that are stable under such acidic and/or photochemical deprotection conditions.

Accordingly, there is a need for hydroxyl-protecting groups that can be removed under mild conditions, and for methods of using such protecting groups. The invention provides such protecting groups and methods. These and other objects and advantages of the invention, as well as additional inventive features, will be apparent from the description of the invention provided herein.

BRIEF SUMMARY OF THE INVENTION

The invention provides a hydroxyl-protected alcohol, which includes a thermolabile 2-pyridyl-substituted hydroxyl-protecting group. In one embodiment, the hydroxyl-protected alcohol is of the formula Pg-O—R, wherein Pg is a protecting group of the formula I:

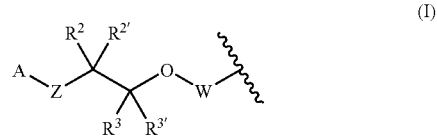

wherein:

A is a 2-pyridyl;

Z is $CH_2$ or $NR^1$;

$R^1$, $R^2$, $R^{2'}$, $R^3$ and $R^{3'}$ are the same or different and each is H, a saturated alkyl, an unsaturated alkyl, an aryl, a saturated alkyl comprising an aryl substituent, or an unsaturated alkyl comprising an aryl substituent;

W is CO, CS, or SO; and

R is the organic residue of the hydroxyl-protected alcohol, wherein the protecting group is thermolabile.

The present invention also provides a method of producing an alcohol comprising heating the hydroxyl-protected alcohol so as to deprotect the hydroxyl-protected alcohol, thereby producing an alcohol, e.g., an alcohol of the formula R—OH (II), wherein R is defined as above. Further in accordance with the present invention, the hydroxyl-protected alcohol can be provided, e.g., from a precursor.

Nucleosides, oligonucleotides, and oligomers comprising one or more oligonucleotides are among the alcohols that can be produced in accordance with the method of the present invention. In one embodiment, the present invention provides a method of producing an oligonucleotide comprising:

(a) reacting a nucleophile with an electrophile to produce an adduct of the formula:

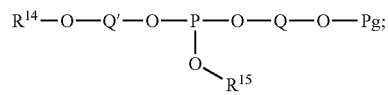

(b) reacting the adduct obtained in step (a) with a reagent selected from the group consisting of oxidizing agents, sulfurizing agents, and selenizing agents to produce a hydroxyl-protected oligonucleotide of the formula:

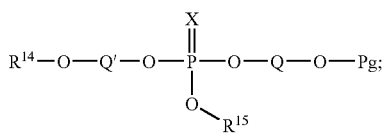

(c) heating the hydroxyl-protected oligonucleotide obtained in step (b) at a temperature effective to cleave Pg to produce a nucleophile of the formula:

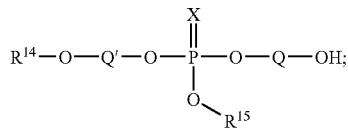

(d) optionally repeating steps (a)-(c) to produce an oligomer of the formula:

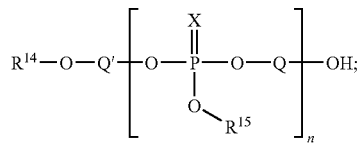

(e) optionally removing $R^{14}$; and
(f) optionally removing $R^{15}$;

wherein:
Pg is a thermolabile hydroxyl-protecting group as defined herein;
n is an integer from 2 to about 300;
$R^{14}$ is a protecting group or a solid support;
$R^{15}$ is a protecting group;
Q and Q' are the same or different (each Q and Q' is independently selected) and each is a nucleoside, an oligonucleotide, or an oligomer comprising a nucleoside; and,
X is O, S or Se.

DETAILED DESCRIPTION OF THE INVENTION

Figure 1:
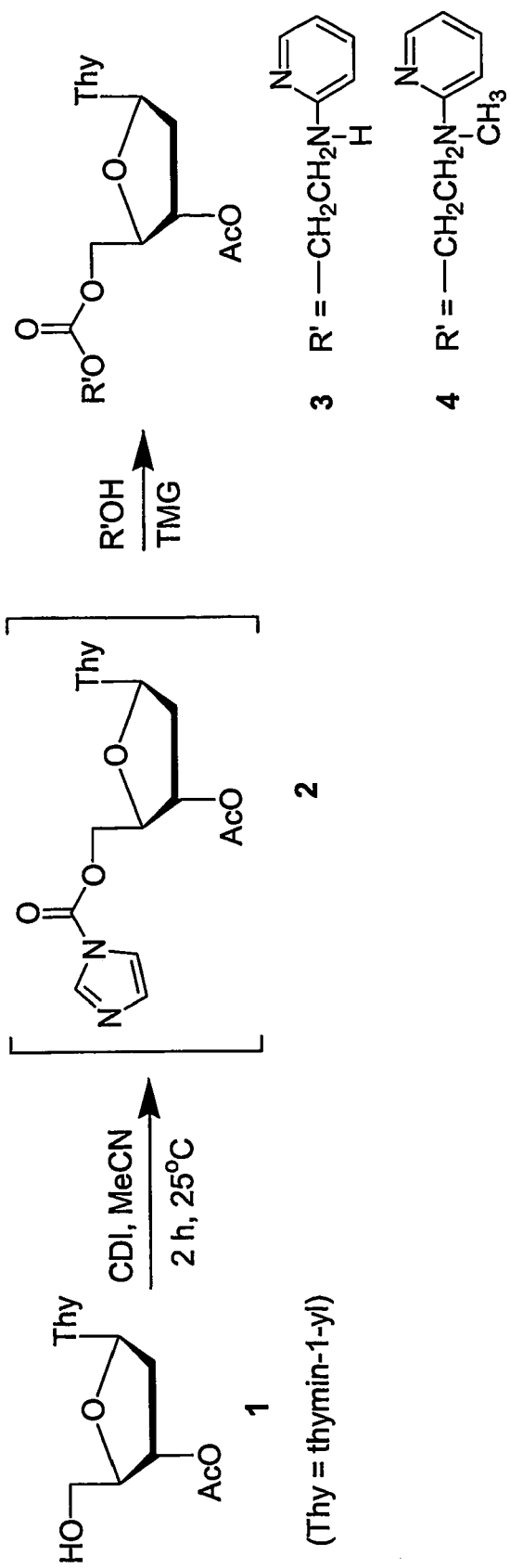
FIG. 1 illustrates the synthesis of a nucleoside in which the 5'-hydroxyl is protected with an exemplary thermolabile hydroxyl-protecting group.

The present invention is predicated on the surprising and unexpected discovery of a novel class of 2-pyridyl-substituted hydroxyl protecting groups that can be efficiently cleaved thermally under mild conditions without the use of harsh chemicals such as, e.g., acids or bases. In one embodiment, the present invention provides a hydroxyl-protected alcohol of the formula Pg-O—R, wherein Pg is a protecting group of the formula I:

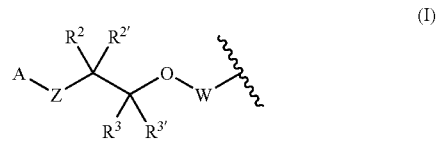

wherein:
A is a 2-pyridyl;
Z is $CH_2$ or $NR^1$;
$R^1$, $R^2$, $R^{2'}$, $R^3$ and $R^{3'}$ are the same or different and each is H, a saturated alkyl, an unsaturated alkyl, an aryl, a saturated alkyl comprising an aryl substituent, or an unsaturated alkyl comprising an aryl substituent;
W is CO, CS, or SO; and
R is the organic residue of the hydroxyl-protected alcohol, wherein the protecting group is thermolabile.

In one embodiment, the protecting group of the present invention comprises a protecting group of formula I, wherein Z is $NR^1$, and wherein $R^1$ is H, an alkyl, or an aryl. Preferably, $R^1$ is H or a saturated alkyl (e.g., methyl). In another embodiment, the protecting group of the present invention is of formula I, wherein Z is $CH_2$.

The thermolabile hydroxyl-protecting group of the present invention can include any suitable 2-pyridyl-substituent. The thermolabile hydroxyl-protecting group of the present invention can include, for example, a protecting group of formula I, wherein A is a 2-pyridyl group of the formula:

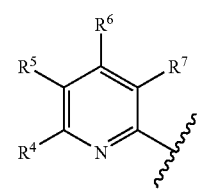

wherein $R^4$, $R^5$, $R^6$, and $R^7$ are the same or different and each is H, an amino, a monoalkylamino, a dialkylamino, a hydroxy, an alkoxy, a halogen, an amide, a saturated alkyl, an unsaturated alkyl, an aryl, a saturated alkyl comprising an aryl, or an unsaturated alkyl comprising an aryl. Although Applicants do not wish to be bound to any particular theory, it is believed that the thermolability of the protecting group of the present invention may be a function of the nucleophilicity of the pyridyl ring. In one respect, the substituents $R^4$, $R^5$, $R^6$, $R^7$, and combinations thereof may be chosen to modulate the nucleophilicity of the 2-pyridyl ring, e.g., so as to modulate the thermolability of the thermolabile protecting group of the present invention. For example, electron-donating substituents, e.g., amino, monoalkylamino, and dialkylamino, may be used as substituents to increase the nucleophilicity of the pyridyl ring, and thereby increase the thermolability of the protecting group. Such electron-donating substituents are believed to be particularly effective at increasing the nucleophilicity of the 2-pyridyl ring when substituted at the 4-position (e.g., $R^6$) and/or at the 6-position (e.g., $R^4$). Of course, there may be applications in which minimizing thermolability is preferred, e.g., so as to allow for thermolytic cleavage at temperatures above ambient temperatures (e.g., about 50° C. or above). In such cases, it may be possible to select a substituent, or a combination of substituents, which renders the 2-pyridyl ring sufficiently nucleophilic to undergo thermolytic cleavage above (and not to an appreciable extent below) certain temperature ranges, e.g., above ambient temperature (e.g., about 50° C. or above). Preferably, the substituents do not undergo side reactions with reactive functional groups, e.g., that may be present on the alcohol organic residue R. For example, when R contains a phosphoramidite linkage, the substituents desirably are selected from among those, which are not reactive with phosphoramidites or precursors thereof.

When $R^1$, $R^2$, $R^{2'}$, $R^3$ or $R^{3'}$ is a saturated alkyl, an unsaturated alkyl, a saturated alkyl comprising an aryl substituent, or an unsaturated alkyl comprising an aryl substituent, the unsaturated alkyl or saturated alkyl can be unsubstituted or substituted with one or more substituents, which are the same or different, selected from the group consisting of a halogen, a saturated alkyl, an unsaturated alkyl, a hydroxyl, an alkoxy, an aryloxy, an aralkoxy, an ester, an amide, a sulfhydryl, an alkyl sulfide, an aryl sulfide, an alkyl sulfoxide, an aryl sulfoxide, an alkyl sulfonyl, an aryl sulfonyl, a keto, a thioketo, a cyano, and a nitro.

When $R^1$, $R^2$, $R^{2'}$, $R^3$ or $R^{3'}$ is an aryl, a saturated alkyl comprising an aryl substituent, or an unsaturated alkyl comprising an aryl substituent, the aryl substituent can be unsubstituted or substituted with one or more substituents, which are the same or different, selected from the group consisting of a halogen, a saturated alkyl, an unsaturated alkyl, a hydroxy, an alkoxy, an aryloxy, an aralkoxy, an ester, an amide, a sulfhydryl, an alkyl sulfide, an aryl sulfide, an alkyl sulfoxide, an aryl sulfoxide, an alkylsulfonyl, an arylsulfonyl, a keto, a thioketo, a cyano, a nitro, an amino, a monoalkylamino, and a dialkylamino.

An exemplary protecting group of the present invention includes a protecting group of formula I, wherein $R^2$ and $R^{2'}$ are H. Another exemplary protecting group of the present invention includes a protecting group of formula I, wherein $R^3$ and $R^{3'}$ are H, or one of $R^3$ and $R^{3'}$ is H and the other is an aryl. Yet another exemplary protecting group of the present invention includes a protecting group of formula I, wherein W is CO. The present invention further provides a precursor of a hydroxyl-protected alcohol of the formula Pg-O—R, wherein Pg and R are as defined herein.

In another embodiment, the present invention provides a 2-(2-pyridyl)aminoethoxycarbonyl-protected alcohol, wherein the 2-(2-pyridyl)aminoethoxycarbonyl group is thermolabile, or a 3-(2-pyridyl) propoxycarbonyl-protected alcohol, wherein the 3-(2-pyridyl)propoxycarbonyl-protecting group is thermolabile. The present invention also provides a precursor of the 2-(2-pyridyl)aminoethoxycarbonyl-protected alcohol of the present invention, or the 3-(2-pyridyl) propoxycarbonyl-protected alcohol of the present invention.

Exemplary protecting groups of the present invention include protecting groups of the formulae:

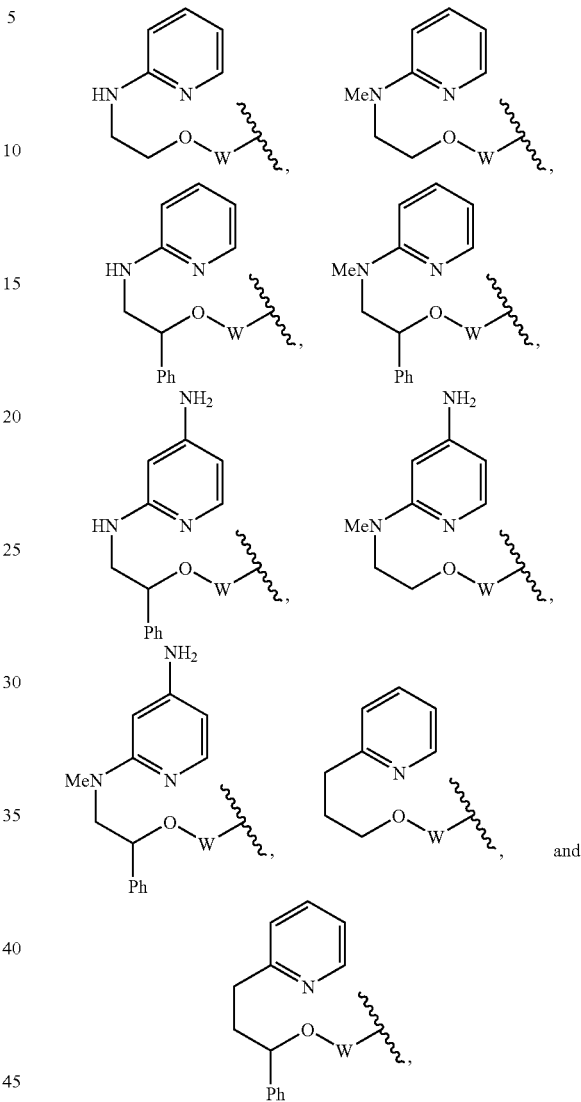

wherein W preferably is CO.

The thermolabile protecting group of the present invention can be used for the protection of any suitable alcohol. Suitable alcohols can range from relatively simple alcohols such as, e.g, low molecular weight aliphatic alcohols, to low molecular weight aromatic alcohols, and the like, to relatively complex alcohols such as, e.g., polyols, sterols, saccharides, nucleic acids, and the like. For instance, the protecting group of the present invention can be used as a hydroxyl-protecting group for nucleosides, oligonucleotides and oligomers that comprise a nucleoside. In one embodiment, the present invention provides a hydroxyl-protected alcohol of the formula R—O-Pg, wherein Pg is as defined herein and R is a nucleoside, an oligonucleotide, or an oligomer comprising a nucleoside. Preferably, R is a nucleoside, an oligonucleotide comprising 2 to about 300 nucleosides, or an oligomer comprising from about 2 to 300 nucleosides. Such R groups can include, for example, residues of the formula:

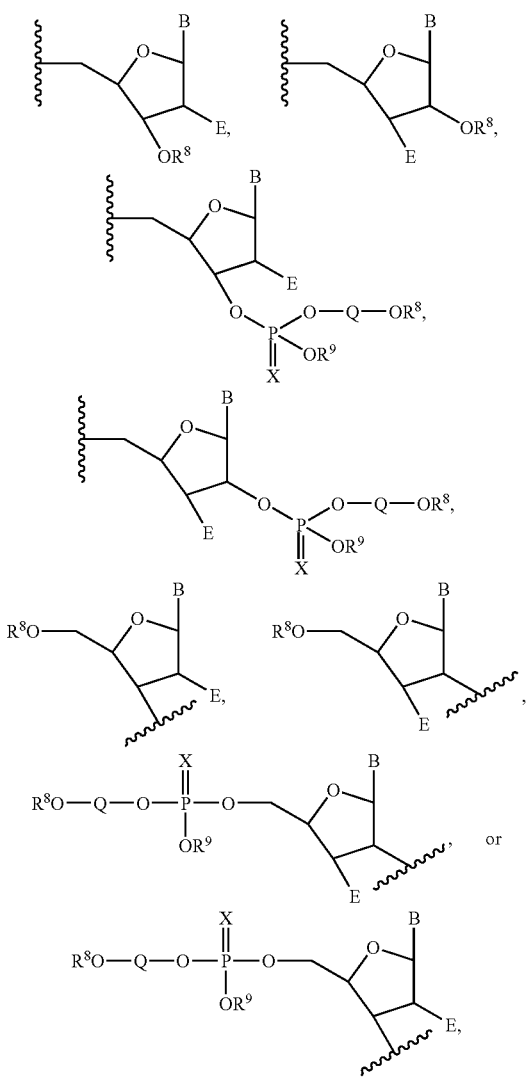

wherein:
Q is a nucleoside, an oligonucleotide, or an oligomer comprising a nucleoside;
X is O, S or Se;
$R^8$ is H, a protecting group, or a solid support;
$R^9$ is H or a protecting group;
B is a labeling group, a saturated alkyl, an unsaturated alkyl, a cycloalkyl, an aryl, a heteroaryl comprising from 5 to about 10 atoms in the ring skeleton thereof, a heterocycloalkyl comprising from 3 to about 10 atoms in the ring skeleton thereof, a saturated alkyl 1 comprising an aryl substituent, an unsaturated alkyl comprising an aryl substituent, an amino, an alkylamino, a dialkylamino, a purine, a pyrimidine, adenine, guanine, cytosine, uracil, or thymine, wherein B is unsubstituted or substituted with one or more substituents, which are the same or different, selected from the group consisting of a nucleobase protecting group, $R^{10}$, $OR^{10}$, $NHR^{10}$, $NR^{10}R^{11}$, N=CH—$NR^{10a}R^{11a}$, N=C(alkyl)-$NR^{10a}R^{11a}$, CN, $NO_2$, $N_3$, and a halogen, wherein $R^{10}$ and $R^{11}$ are the same or different and each is H, a saturated alkyl, an unsaturated alkyl, a keto, or a thioketo, and $R^{10a}$ and $Ru^{11a}$ are the same or different and each is a saturated alkyl or an unsaturated alkyl, or, $R^{10a}$ and $R^{11a}$, together with the nitrogen atom to which they are bonded, form a heterocycle containing 3 to about 7 atoms in the ring skeleton thereof; and
E is H, a halogen, $OR^{12}$, $NHR^{12}$, or $NR^{12}R^{13}$, wherein $R^{12}$ and $R^{13}$ are the same or different and each is H, a protecting group, a saturated alkyl, an unsaturated alkyl, a keto or a thioketo.

An exemplary R group can include, more particularly, a nucleoside, an oligonucleotide comprising from 2 to about 300 nucleosides, or an oligomer comprising from 2 to about 300 nucleosides. For example, R can be of the formula:

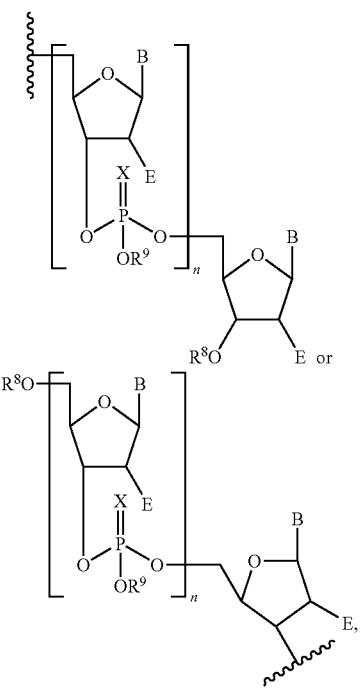

wherein n is an integer from 0 (in which case R is a nucleoside) to, about 300.

Suitable B substituents can include heterocycles that are commonly used in oligonucleotide synthesis such as, for example, substituents selected from the group consisting of a purine, a pyrimidine, adenine, guanine, cytosine, uracil, and thymine. Suitable nucleosides can include nucleosides that are commonly used in oligonucleotide synthesis such as, for example, nucleosides of the formula:

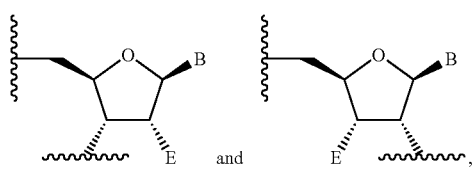

wherein B and E are as defined herein.

The hydroxyl-protected alcohol should be heated to a temperature effective to cleave the thermolabile hydroxyl-protecting group (preferably so as to deprotect the alcohol). Desirably, the temperature effective to cleave thermally the hydroxyl-protecting group is lower than the temperature at which the alcohol (the protected alcohol or the unprotected alcohol) degrades in the reaction system. It will be appreciated that the temperature effective to cleave thermally the hydroxyl-protecting group can vary depending on the structure of the protecting group, the structure of the alcohol that is protected, and environmental factors such as, e.g., solvent, pH, pressure, concentration, other reactants, other reagents, by-products, and the like. It will also be appreciated that the degradation temperature of the alcohol (protected or unprotected) also can vary depending on the structure of the alcohol and environmental factors such as, e.g., solvent, pH, pressure, concentration, other reactants, other reagents, by products, and the like.

Any suitable temperature can be used in accordance with the deprotection method of the present invention. For example, the temperature effective to cleave thermally the hydroxyl-protecting group can range from about 20-150° C., from about 30-120° C., from about 40-100° C, from about 50-90° C., from about 60-90° C., from about 70-90° C., from about 30-50° C., and the like.

If desired, the deprotection method of the present invention can be carried out in a fluid medium, e.g., in the presence of a solvent. Suitable solvents can include, for example, organic solvents and aqueous solvents. Organic solvents can include, for example, alcohols, aliphatic hydrocarbons, aromatic hydrocarbons, ketones, ethers, and the like. Suitable organic solvents include acetonitrile, carbon tetrachloride, dioxane, tert-butanol, ethanol, and combinations thereof. Aqueous solvents can include, for example, water, mixtures of water and an organic solvent (e.g., water/alcohol mixtures, water/acetonitrile mixtures, water/acetone mixtures), and the like. Preferably, the solvent is an aqueous solvent. Exemplary aqueous solvents include water, water/acetonitrile mixtures, water/ethanol mixtures, and the like.

In some instances, it may be desirable to perform the method of the present invention within a preferred pH range, particularly for pH-sensitive compounds. When the alcohol produced in accordance with the method of the present invention is a nucleoside, an oligonucleotide, or an oligomer comprising a nucleoside, the method preferably is carried out from about pH 6-8, more preferably from about pH 6.5-7.5, and still more preferably from about pH 7-7.5. If desired, a suitable buffer (e.g., a phosphate buffer such as PBS or the like) can be used to stabilize the pH.

The present invention further provides a method of producing an alcohol, which method comprises heating the hydroxyl-protected alcohol of the present invention so as to deprotect the hydroxyl-protected alcohol, thereby producing an alcohol, such as, for example, an alcohol of the formula R—OH (II), wherein R is as defined herein. The method of the present invention can further comprise providing the hydroxyl-protected alcohol. For example, the hydroxyl-protected alcohol can be provided by way of a precursor, e.g., by forming the hydroxyl-protected alcohol from a precursor. Forming (e.g., producing) the hydroxyl-protected alcohol can be accomplished using any suitable method, e.g., by converting a precursor to the hydroxyl-protected alcohol synthetically (e.g., chemically, photolytically, electrochemically, thermally, or the like), naturally, or by any other suitable means. The hydroxyl-protected alcohol of the present invention also can be provided, e.g., by delivery to a production facility, commercial purchase, or as an intermediate in an array synthesis. The method of the present invention also can include synthetically modifying the hydroxyl-protected alcohol of the present invention prior to deprotection. Such synthetic modifications can include, for example, oxidation reactions, reduction reactions, rearrangement reactions, coupling reactions, fragmentation reactions, addition reactions, complexation reactions, catalytic reactions, displacement reactions, enzymatic reactions, and the like.

For example, the hydroxyl-protected alcohol can be provided by reducing a precursor of the formula:

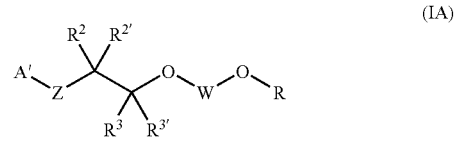

wherein
A' is a 2-pyridyl comprising a nitro-substituent, a 2-pyridyl-1-oxide, or a 2-pyridyl-1-oxide comprising a nitro substituent;
Z is $CH_2$ or $NR^1$,
$R^1$, $R^2$, $R^{2'}$, $R^3$ and $R^{3'}$ are the same or different and each is H, a saturated alkyl, an unsaturated alkyl, an aryl, a saturated alkyl comprising an aryl substituent, or an unsaturated alkyl comprising an aryl substituent,
W is CO, CS, or SO; and
R is the organic residue of the hydroxyl-protected alcohol, so as to reduce the pyridine-1-oxide to the corresponding pyridine ring, or so as to reduce the nitro-pyridine or nitro-pyridine-1-oxide to the corresponding amino-substituted pyridine ring, thereby producing a hydroxyl-protecting group, which is thermolabile.

In one embodiment, A' of the precursor is selected from the group consisting of:

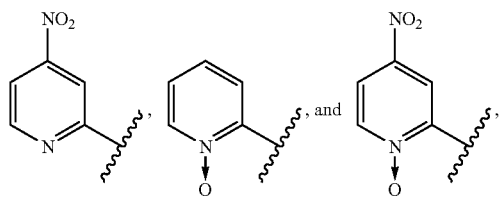

wherein Z, $R^1$, $R^2$, $R^{2'}$, $R^3$, $R^{3'}$, W, and R are as described herein. An exemplary the precursor is of the formula:

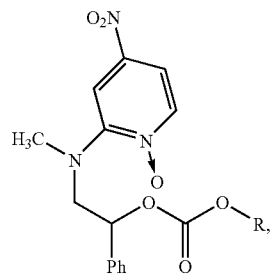

wherein R is as described herein. In this instance, reduction of the nitro and 1-oxide substituents, to produce the corresponding 4aminopyridine, generates a hydroxyl-protecting group, which can be easily cleaved thermolytically in accordance with the method of the present invention, to produce the corresponding alcohol (ROH).

Thus, in one aspect, the present invention provides a method of producing an alcohol, which method comprises heating a 2-(2-pyridyl)aminoethoxycarbonyl-protected alcohol so as to deprotect the alcohol. The 2-(2-pyridyl)aminoethoxycarbonyl protecting group can include any suitable 2-(2-pyridyl)aminoethoxycarbonyl, such as, for example, a 2-(2-pyridyl)aminoethoxycarbonyl protecting group selected from the group consisting of:

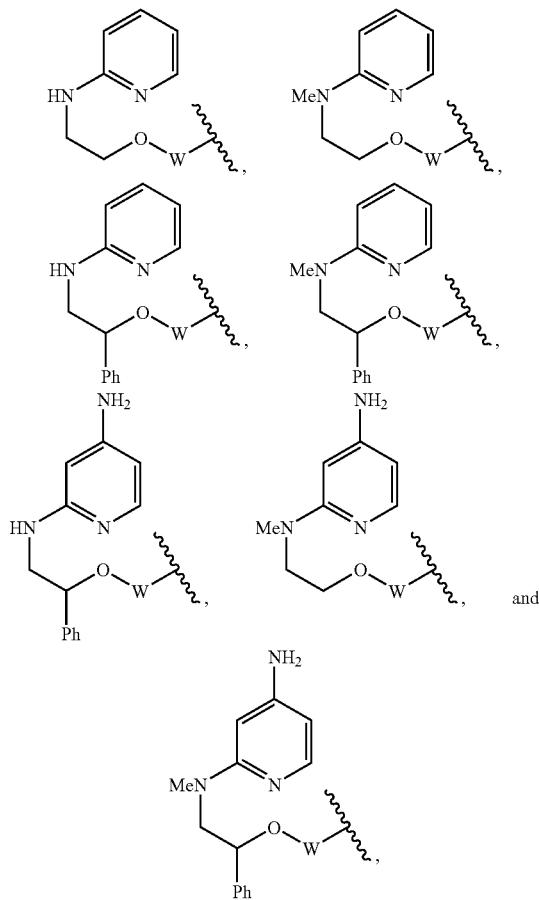

and wherein W preferably is CO. In another aspect, the present invention provides a method of producing an alcohol, which method comprises heating a 3-(2-pyridyl)propoxycarbonyl-protected alcohol so as to deprotect the alcohol. The 3-(2-pyridyl)propoxycarbonyl protecting group can include any suitable 3-(2-pyridyl)propoxycarbonyl, such as, for example, a protecting group of the formula:

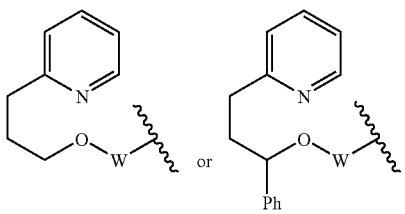

wherein W preferably is CO. The 2-(2-pyridyl)aminoethoxycarbonyl-protected or 3-(2-pyridyl)propoxycarbonyl-protected alcohol of the present invention can be used to produce an alcohol such as, for example, a nucleoside, an oligonucleoside, or an oligomer comprising a nucleoside. Preferably, the alcohol is a nucleoside, an oligonucleotide comprising from 2 to about 300 nucleosides, or an oligomer comprising from 2 to about 300 nucleosides.

The compounds and methods of the present invention further can be used, for example, in oligomer synthesis, e.g., oligonucleotide synthesis. In one embodiment, the present invention provides a method of producing an oligonucleotide, which method comprises:

(a) reacting a nucleophile with an electrophile to produce an adduct of the formula:

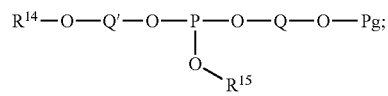

(b) reacting the adduct obtained in step (a) with a reagent selected from the group consisting of oxidizing agents, sulfurizing agents, and selenizing agents to produce a hydroxyl-protected oligonucleotide of the formula:

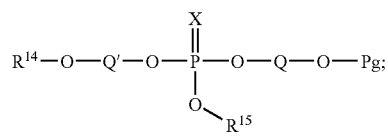

(c) heating the hydroxyl-protected oligonucleotide obtained in step (b) at a temperature effective to cleave Pg to produce a nucleophile of the formula:

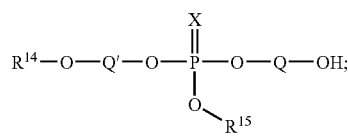

(d) optionally repeating steps (a)-(c) to produce an oligomer of the formula:

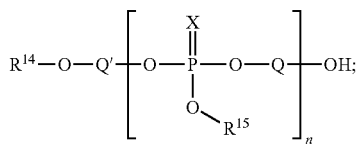

(e) optionally removing $R^{14}$; and
(f) optionally removing $R^{15}$;

wherein:
Pg is a thermolabile hydroxyl-protecting group as defined herein;
n is an integer from 2 to about 300;
$R^{14}$ is a protecting group or a solid support;
$R^{15}$ is a protecting group;
Q and Q' are the same or different (each Q and Q' is independently selected) and each is a nucleoside, an oligonucleotide (e.g., an olgonucleotide comprising from 2 to about 300 nucleosides), or an oligomer comprising a nucleoside (e.g. an oligomer comprising from 2 to about 300 nucleosides); and, X is O, S or Se.

In another embodiment, the present invention provides a method of producing an oligonucleotide, which method comprises:

(a) reacting a nucleophile with an electrophile to produce an adduct of the formula:

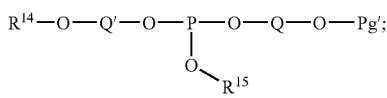

(b) reacting the adduct obtained in step (a) with a reagent selected from the group consisting of oxidizing agents, sulfurizing agents, and selenizing agents to produce a hydroxyl-protected oligonucleotide of the formula:

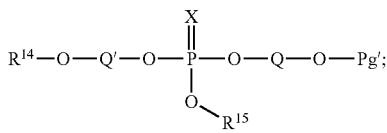

(c) subjecting the hydroxyl-protected oligonucleotide obtained in step (b) to reduction conditions to produce a hydroxyl-protected oligonucleotide of the formula:

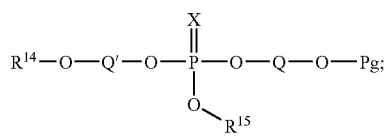

(d) thermally cleaving Pg to produce a nucleophile of the formula;

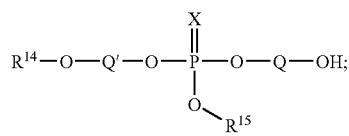

(e) optionally repeating steps (a)-(d) to produce an oligomer of the formula:

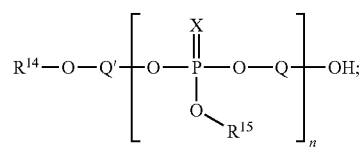

(f) optionally removing $R^{14}$; and
(g) optionally removing $R^{15}$;

wherein:
Pg' is a hydroxyl-protecting group of the formula:

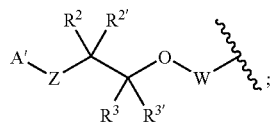

wherein A' is a 2-pyridyl comprising a nitro substituent, a 2-pyridyl-1-oxide, or a 2-pyridyl-1-oxide comprising a nitro substituent; and Pg, A, Z. $R^1$, $R^2$, $R^{2'}$, $R^3$, $R^{3'}$, W, n, $R^{14}$, $R^{15}$, Q, Q', X are as defined herein, wherein the reduction in step (c) reduces the 1-oxide substituent of A' (e.g., to produce the corresponding pyridine ring), the nitro substituent of A' (e.g., to produce the corresponding amino-substituted pyridine), or the 1-oxide and nitro substituents on A' (e.g., to produce the corresponding amino-substituted pyridine).

The thermolytic cleavage of the hydroxyl-protecting group (e.g., Pg) can be carried out in accordance with the methods of the present invention described herein. Preferably, the temperature effective to thermally cleave Pg, in accordance with the method of the present invention, is below about 100° C. More preferably, the thermolytic cleavage is carried out at a temperature of from about 40-90° C., and even more preferably from about 50-90° C. In a preferred embodiment, the thermolytic cleavage is carried out in a solvent, which is preferably an aqueous solvent. Exemplary aqueous solvents include water, water/acetonitrile mixtures, water/ethanol mixtures, and the like. Desirably, a suitable buffer, e.g., a phosphate buffer, is used in the thermolytic cleavage. The compounds and methods of the present invention also can be used in accordance with the methods described in Applicants' copending International Patent Application No. PCT/US02/38400.

The term "saturated alkyl" means a straight- or branched-chain saturated alkyl containing, e.g., from 1 to about 20 carbon atoms, for example, from 1 to about 10 carbon atoms, from 1 to about 8 carbon atoms, or from 1 to about 6 carbon atoms. Examples of saturated alkyls include methyl, ethyl, propyl, isopropyl, n-butyl, sec-butyl, octadecyl, and the like. Saturated alkyl substituents can be unsubstituted or substituted, for example, with at least one substituent selected from the group consisting of a halogen, a nitro, an amino, a hydroxyl, an alkoxy, an aryloxy, an aralkoxy, an ester, an amide, a sulfhydryl, an alkyl sulfide, an aryl sulfide, an alkyl sulfoxide, an aryl sulfoxide, an alkyl sulfonyl, an aryl sulfonyl, a keto, a thioketo, an alkyl, a cyano, and the like.

The term "unsaturated alkyl" means an unsaturated alkyl (straight- or branched-chain), as defined herein, in which at least one single carbon-carbon bonds thereof is instead a multiple bond, for example, a double bond or a triple bond. Unsaturated alkyls include alkenyls and alkynyl, as well as substituents that have a combination of double and triple bonds. The term "alkenyl" means a straight- or branched-chain alkenyl having one or more double bonds. An alkenyl can contain, e.g., from 2 to about 20 carbon atoms, for example, from 2 to about 10 carbon atoms, from 2 to about 8 carbon atoms, or from 2 to about 6 carbon atoms. Examples of alkenyls include vinyl, allyl, 1,4-butadienyl, isopropenyl, and the like. The term "alkynyl" means a straight- or branched-chain alkynyl having one or more triple bonds. An alkynyl can contain, e.g., from 2 to about 20 carbon atoms, for example, from 2 to about 10 carbon atoms, from 2 to about 8 carbon atoms, or from 2 to about 6 carbon atoms. Examples of alkynyl include ethynyl, propynyl (propargyl), butynyl, and the like. Unsaturated alkyl substituents can be unsubstituted or substituted, for example, with at least one substituent selected from the group consisting of a halogen, a nitro, an amino, a hydroxyl, an alkoxy, an aryloxy, an aralkoxy, an ester, an amide, a sulfhydryl, an alkyl sulfide, an aryl sulfide, an alkyl sulfoxide, an aryl sulfoxide, an alkyl sulfonyl, an aryl sulfonyl, a keto, a thioketo, an alkyl, a cyano and the like.

The term "aryl" means an aromatic carbocyclic radical, as commonly understood in the art, and includes monocyclic and polycyclic aromatics. The aryl substituent preferably comprises 6-14 carbon atoms in the carbocyclic skeleton thereof. Examples of aryl substituents include, but are not limited to, phenyl, naphthyl and the like, which are unsubstituted or substituted with one or more substituents selected from the group consisting of a halogen, a saturated alkyl, an unsaturated alkyl, a hydroxyl, an alkoxy, an aryloxy, an aralkoxy, an ester, an amide, a sulfhydryl, an alkyl sulfide, an aryl sulfide, an alkyl sulfoxide, an aryl sulfoxide, an alkylsulfonyl, an arylsulfonyl, a keto, a thioketo, a cyano, a nitro, an amino, an alkylamino, a dialkylamino, and the like.

A saturated alkyl comprising an aryl substituent means an alkyl substituent in which at least one hydrogen atom thereof is substituted with an aryl substituent (an aralkyl). Examples of saturated alkyls comprising an aryl substituent include, but are not limited to, benzyl, phenethyl, 2-phenyl-1-propyl, 3,4diphenylbutyl and the like.

An unsaturated alkyl comprising an aryl substituent means an unsaturated alkyl substituent in which at least one hydrogen atom thereof is substituted with an aryl (an aralkenyl or an aralkinyl). Examples of unsaturated alkyls comprising an aryl substituent include, but are not limited to, 2-phenylethenyl, 2-phenylethinyl, 4-naphthyl-2-butynyl and the like.

The term "alkoxy" means a saturated alkyl or an unsaturated alkyl in which at least one hydrogen atom thereof is substituted with an oxygen atom. Examples of alkoxy substituents include, but are not limited to, methoxy, ethoxy, isopropoxy, 2-butenyloxy, and the like.

The term "aryloxy" means an aryl in which at least one hydrogen atom thereof is substituted with an oxygen atom. Examples of aryloxy substituents include, but are not limited to, phenoxy, naphthoxy and the like.

The term "aralkoxy" means an aralkyl, an aralkenyl or an aralkinyl in which at least one hydrogen atom thereof is substituted with an oxygen atom. Examples of aralkoxy substituents include, but are not limited to, benzyloxy, 4-phenyl-n-butoxy, 4-phenyl-2-butene-1-yloxy, and the like.

The term "ester" means a carboxylic acid or an analog thereof in which an acidic proton is replaced by an organic radical such as, for example, a saturated alkyl, an unsaturated alkyl, an aryl, an aralkyl or the like. Examples of esters include, but are not limited to, alkyl carboxylates (e.g., ethoxycarbonyl and tert-butyloxycarbonyl), unsaturated alkyl carboxylates (e.g., allyloxycarbonyl), aryl carboxylates (e.g., phenoxycarbonyl and benzyloxycarbonyl) and thioesters (e.g., benzylthiocarbonyl), and the like.

The term "amide" means aminocarbonyl and analogous substituents. Examples of amides include, but are not limited to, N-alkyl amides (e.g., ethylaminocarbonyl, diethylaminocarbonyl, and tert-butylaminocarbonyl), unsaturated N-alkyl amides and analogous substituents (e.g., allylaminocarbonyl), N-aryl amides and analogous substituents (e.g., phenylaminocarbonyl and benzylaminocarbonyl) and thioamides (e.g., benzylaminothiocarbonyl), and the like.

The term "alkyl sulfide" means a saturated or an unsaturated alkyl in which at least one hydrogen atom thereof is substituted with a sulfur atom. Examples of alkyl sulfides include, but are not limited to, methylthio, ethylthio, isopropylthio, 2-butenylthio, and the like.

The term "aryl sulfide" means an aryl in which at least one hydrogen atom thereof is substituted with a sulfur atom. Examples of aryl sulfides include, but are not limited to, phenylthio, naphthylthio and the like.

The term "alkyl sulfoxide" means a saturated or an unsaturated alkyl in which at least one hydrogen atom thereof is substituted with a sulfoxide (SO). Examples of alkyl sulfoxides include, but are not limited to, methylsulfoxy, sthylsulfoxy, isopropylsulfoxy, 2-butenylsulfoxy, and the like.

The term "aryl sulfoxide" means an aryl in which at least one hydrogen atom thereof is substituted with a sulfoxide. Examples of aryl sulfoxides include, but are not limited to, phenylsulfoxy, naphthylsulfoxy and the like.

The term "alkylsulfonyl" means a saturated or an unsaturated alkyl in which at least one hydrogen atom thereof is substituted with a sulfonyl ($SO_2$). Examples of alkylsulfonyls include, but are not limited to, methylsulfonyl, ethylsulfonyl, isopropylsulfonyl, 2-butenylsulfonyl, and the like.

The term "arylsulfonyl" means an aryl in which at least one hydrogen atom thereof is substituted with a sulfonyl. Examples of arylsulfonyl substituents include, but are not limited to, phenylsulfonyl, naphthylsulfonyl and the like.

The term "keto" means a carbonyl, which is substituted with an organic radical such as, for example, a saturated alkyl, an unsaturated alkyl, an aryl, an aralkyl, or the like. Examples of keto substituents include, but are not limited to, alkylcarbonyls (e.g., ethylcarbonyl and tert-butylcarbonyl), unsaturated alkyl carbonyls (e.g., allylcarbonyl), aryl carbonyls (e.g., phenylcarbonyl and benzylcarbonyl), and the like.

The term "thioketo" means a keto in which the carbonyl oxygen is substituted with a sulfur atom. Examples of thioketo substituents include, but are not limited to, alkyl thiocarbonyls (e.g., ethyl thiocarbonyl and tert-butyl thiocarbonyl), unsaturated alkyl thiocarbonyls (e.g., allyl-thiocarbonyl), aryl thiocarbonyls (e.g., phenyl thiocarbonyl and benzyl thiocarbonyl), and the like.

The term "alkylamino" means an amino, which is substituted with one saturated or unsaturated alkyl substituent. Examples of alkylamino substituents include, but are not limited to, methylamino, ethylamino, isopropylamino, 2-butenylamino, and the like.

The term "dialkylamino" means an amino which is substituted with two alkyl substituents, which are the same or different and which can be saturated or unsaturated. Examples of dialkylamino substituents include dimethylamino, diethylamino, ethylisopropylamino, diisopropylamino, di-2-butenylamino and the like.

The term "cycloalkyl" means a monocycloalkyl or a polycycloalkyl which comprises one or more aliphatic carbocyclic rings, which are the same or different. Typically, the cycloalkyl has from 3 to about 10 carbon atoms in the carbocyclic skeleton of each ring. Preferably, the cycloalkyl has from about 4-7 carbon atoms, more preferably from about 5-6 carbons atoms in each ring. Examples of monocyclic cycloalkyl include cyclopropyl, cyclobutyl, cyclopentyl, cyclohexyl, cyclohexenyl, cycloheptyl, cyclodecyl, and the like. Examples of polycyclic cycloalkyls include decahydronaphthyl, bicyclo[5.4.0]undecyl, adamantyl, and the like.

The terms heterocycle and heterocyclic refer to heterocycloalkyls and heteroaryls. The term "heterocycloalkyl" means a cycloalkyl in which at least one carbon in the ring skeleton thereof is substituted with a heteroatom such as, for example, O, N, S, an oxide of N, an oxide of S, and the like. The heterocycloalkyl optionally has one or more double bonds within one or more of its rings, and may include a non-aromatic or an aromatic ring. The heterocycloalkyl preferably has from 3 to about 10 atoms (members) in the skeleton of each ring, more preferably from about 5-10 atoms, still more preferably from about 4-7 atoms, and most preferably 5-6 atoms. Examples of heterocycloalkyls include epoxy, aziridinyl, oxetanyl, tetrahydrofuranyl, ribose, dihydrofuranyl, piperidinyl, piperazinyl, pyranyl, morpholinyl, and the like.

The term "heteroaryl" means an aromatic heterocyclic ring as commonly understood in the art, including monocyclics such as, for example, imidazolyl, thiazolyl, pyrazolyl, pyrrolyl, furanyl, pyrazolinyl, thiophenyl, oxazolyl, isoxazolyl, pyridinyl, pyridonyl, pyrrolidinyl, cytosinyl, 5-methylcytosinyl, thyminyl, pyrazinyl, and triazinyl, and polycyclics such as, for example, quinolinyl, isoquinolinyl, indolyl, purinyl, adeninyl, guaninyl, $N^6$-methyladeninyl, benzothiazolyl, and the like. The heteroaryl can be unsubstituted or substituted with one or more substituents, which are the same or different, selected from the group consisting of the aryl substituents described herein, and the like. The heteroaryl preferably has from 3 to about 10 atoms (members) in the ring skeleton of each ring, more preferably from about 4-7 atoms, and most preferably 5-6 atoms.

It will be appreciated that the heterocycloalkyl and heteroaryl substituents can be bonded via a heteroatom, such as nitrogen (e.g., 1-imidazolyl), or via a carbon atom (e.g., 2-imidazolyl and 4-thiazolyl)l It will also be appreciated that the heteroaryls are not necessarily "aromatic" to the same extent as a benzene ring, although heteroaryls can nonetheless demonstrate physical and chemical properties associated with aromaticity, as commonly understood in the art.

The term "nucleoside" includes naturally occurring and modified nucleosides, including all forms of furanosides found in nucleic acids. Naturally occurring nucleosides include, for example, adenosine, guanosine, cytidine, thymidine, and uridine.

Nucleoside "derivatives" or "analogs" include synthetic nucleosides and intermediates that are useful for the preparation thereof, e.g., as described herein. Nucleoside derivatives also include nucleosides having modified base moieties, with or without protecting groups. Such analogs include, for example, deoxyinosine, 2,6-diaminopurine-2'-deoxyriboside, 5-methyl-2'-deoxycytidine, and the like. The base rings most commonly found in naturally occurring nucleosides are purine and pyrimidine rings. Naturally occurring purine rings include, for example, adenine, guanine, and $N^6$-methyladenine. Naturally occurring pyrimidine rings include, for example, cytosine, thymine, and 5-methylcytosine. The compounds and methods of the present invention include such base rings and synthetic analogs thereof, as well as unnatural heterocycle-substituted base sugars, acyclic-substituted base sugars, and the like. Moreover, nucleoside derivatives include other purine and pyrimidine derivatives, for example, halogen-substituted purines (e.g., 6-fluoropurine), halogen-substituted pyrimidines (e.g., 5-fluoro uracil), $N^6$-ethyladenine, $N^6$-(alkyl)-cytosines, 5-ethylcytosine, and the like.

The term "oligonucleotide" includes oligomers (e.g., linear oligomers) of natural or modified nucleosides, modified oligonucleotides, and the like. Oligonucleotides include deoxyribonucleosides, ribonucleosides, anomeric forms thereof, and the like. Oligonucleotides typically are linked by one or more phoshodiester bonds or equivalents thereof, ranging in size from a few monomeric units (e.g., 2-4) to several hundred monomeric units. Exemplary oligonucleotides that can be used in accordance with the present invention include oligomers of naturally-occurring nucleosides, e.g., ranging in length from about 12 to about 60 monomeric units, or from about 15 to about 30 monomeric units. Whenever an oligonucleotide is represented by a sequence of letters, such as "AGTC" it will be appreciated that the nucleotides are in the 5'- to-3'-orientation from left to right.

In accordance with the present invention, Q and/or Q' can be a natural nucleoside or a modified/unnatural nucleoside. Q and/or Q' also can be an oligomer comprising one or more natural or modified/unnatural nucleosides. Modified nucleosides can be obtained, for example, by any suitable synthetic method known in the art for preparing nucleosides, derivatives, or analogs thereof. Modified nucleosides include, but are not limited to, chemically modified nucleosides used as building blocks for "labeled" oligonucleotides, or suitable precursors or analogs used in the preparation of such modified nucleosides. Various chemically modified nucleosides are described, for example, in Smith et al., *Nucleosides & Nucleotides*, 15(10), 1581-1594 (1996) ("Smith et al."). Smith et al. describes the synthesis of nucleosides (and oligomers which include such nucleosides) in which the base ring is replaced by a carboxylic acid. Various "labeling" groups (e.g., biotin, cholesterol, fluorenylmethoxycarbonyl (Fmoc), and trifluoroacetyl) can be appended to the carboxylic acid, e.g., via a modified amide linker. Modified nucleosides also include other chemically modified nucleosides, for example, nucleosides described in Smith et al. in which the base ring is replaced by a hydroxyethyl, a cyano, a carboxylic acid (including esters and amides thereof), or the like. Modified nucleosides further include nucleosides in which the base ring is replaced by a cyclic substituent, for example, an aryl, a cycloalkyl, a heterocycloalkyl, a heteroaryl (other than a base naturally occurring in nucleosides), or the like.

Q and Q' also include oligonucleotides, which can be natural or modified. Modified oligonucleotides include, for example, oligonucleotides containing a modified nucleoside, oligonucleotides containing a modified internucleotide linkage, oligonucleotides having any combination of modified nucleosides and internucleotide linkages (even if a natural nucleoside is present in the oligomer chain), or the like. Oligonucleotides, which include one or more nucleosides that are connected via modified internucleotide linkages, are described, for example, in Waldner et al., *Bioorg. Med. Chem. Letters*, 6, 19, 2363-2366 (1996) ("Waldner et al."), which describes the synthesis of oligonucleotides containing various amide internucleotide linkages.

The term "oligomer comprising a nucleoside" means an oligomer in which at least one of the monomeric units comprises one or more nucleosides, and at least one of the other monomeric units is not a nucleoside. For example, one of the monomeric units in the oligomer can be an amino acid, an organic spacer (e.g., an aliphatic spacer, an aromatic spacer, an alkylene glycol, a carbohydrate (e.g., a sugar), or the like. Moreover, one or more of the non-nucleoside units of the oligomer can be oligomeric, for example, a peptide, an oligosaccharide, a polyalkylene glycol, or the like.

It will be appreciated that protecting groups (sometimes referred to as blocking groups), other than the thermolabile protecting group of the present invention, e.g., standard protecting groups for organic synthesis, can be utilized in accordance with the present invention. Protecting groups can include substituents, functional groups, salts, ligands, and the like, which are bonded (e.g., via covalent bond, ionic bond, complex, or the like) to a potentially reactive functional group. As indicated above, protecting groups can be used to prevent a potentially reactive functional group from reacting under certain reaction conditions. Preferably, the protecting group is stable under the reaction conditions employed, and is removable under mild deprotection conditions. It will be appreciated that protecting groups should be chosen based on the type of substituent that is protected, the structure of the molecule for which the protecting group is used, the reaction conditions used, the type of solvent used, the conditions required for removing the protecting group, and the like. One of skill in the art may choose from among different protecting groups to protect functional groups such as, e.g., phosphites, phosphates, amines, thiols, hydroxyls, and the like. Reaction conditions that influence the choice of protecting group can typically include the pH, the temperature, the relative reactivities of the reactants and/or products, and the like.

Protecting groups for hydroxyls can include, for example, silyl ethers (e.g., trimethylsilyl, triethylsilyl, tert-butyldimethylsilyl, tert-butyldiphenylsilyl, dimethylphenylsilyl, and diphenylmethylsilyl), benzyl carbonates, trityl, monomethoxytrityl, dimethoxytrityl, esters (e.g., acetate, benzoate, and the like), pixyl, tert-butyloxycarbonyl, 9-fluorenylmethyloxycarbonyl (Fmoc), a tetrahydropyranyl group, photolabile protecting groups and the like. When the hydroxyl is a sugar hydroxyl, suitable protecting groups can include, for example, pixyl, acetyl, 9-fluorenylmethyloxycarbonyl (Fmoc), t-butyldimethylsilyl (CBDMS), trityl, monomethoxytrityl ("MMT" or "MMTr"), dimethoxytrityl ("DMT" or "DMTr"), and the like. Protecting groups for nitrogen include, for example, amides (e.g., trifluoroacetyl, acetyl, phenoxyacetyl, benzoyl, and isobutyryl), carbamates (e.g., tert-butyloxycarbonyl, (4-nitrophenyl)ethyloxycarbonyl, and N-benzyloxycarbonyl), trityl, amidines and the like. These are defined in the literature: see, e.g., Iyer, *Current Protocols in Nucleic Acid Chemistry*, Vol. 1 (Beaucage S. L., Bergstrom, D. E., Glick, G. D. Jones R. A. eds); John Wiley and Sons: New York, 2000, pp. 2.1.1-2.1.17; Beaucage, et al., *Tetrahedron*, 48, 2223-2311 (1992); and McBride et al., *J. Am. Chem. Soc.*, 108, 2040-2048 (1986).

Suitable internucleosidic phosphorus protecting groups can include, for example, those described in U.S. Pat. Nos. 4,417,046, 5,705,621, 5,571,902, and 5,959,099. Suitable internucleosidic phosphorus protecting groups also can include those obtained from oligonucleotide synthesis using N-acylphosphoramidite precursors, e.g., as described in International Patent Application Publication No. WO 00/56749. Suitable internucleosidic phosphorus protecting groups also can include thermolabile internucleosidic phosphorus protecting groups as described in U.S. patent application No. 09/792,799 (filed on Feb. 23, 2001);. Grajkowski et al., *Organic Lett.* 3, 1287-1290 (2001); and Wilk et al. *Tetrahedron Lett.*, 42, 5635-5639 (2001).

Suitable protecting groups also can include, for example, 2-[N,N-(dialkylamino)oxy]ethyl (Prakash et al., *Org. Lett.*, 2, 2995-3998 (2000)), a (2-methoxy)ethoxy (Martin, *Helv. Chim. Acta.*, 78, 486-504 (1995)), triisopropylsilyloxymethyl, protecting groups defined by Wincott, *Current Protocols in Nucleic Acid Chemistry, Vol.* 1 (Beaucage S. L., Bergstrom, D. E., Glick, G. D. Jones R. A. eds); and John Wiley and Sons: New York, 2000, pp. 3.5.1-3.5.12, and the like.

Any suitable solid support can be used in accordance with the present invention. Solid supports are commonly known in the art and include, for example, organic solid supports (e.g., crosslinked polystyrene), inorganic solid supports (e.g., silica supports), and like. Preferably, the solid support is an inorganic support, which is more preferably a silica support. It will be appreciated that the solid support can include linkers, spacers, arms, and other moieties (organic and inorganic moieties) known in the art for manipulating attachment to a solid support. It will also be appreciated that the solid support can be bonded to the molecule directly, without the use of linkers, spacers, arms, or other connecting moieties. Some aspects of the invention are common with known approaches to solid phase synthesis of oligonucleotides, for example, selection of suitable protecting groups, selection of suitable solid phase supports, and the like. Consequently, considerable guidance in making such selections in the context of the present invention can be found in literature, e.g. Beaucage et al., *Tetrahedron*, 49, 6123-6194 (1993).

Oxidizing agents that can be used in accordance with the present invention include any suitable reagent that can oxidize a tricoordinated phosphorus atom, particularly a phosphite, to provide a phosphorus atom having a valence of greater than three, preferably a tetracoordinated phosphorus atom such as, for example, a phosphate, or an equivalent thereof Suitable oxidizing agents include, for example, $I_2/H_2O$, peroxides, such as tert-butylhydrogen peroxide, and the like.

Sulfurizing agents that can be used in accordance with the present invention include any suitable reagent that can sulfurize a tricoordinated phosphorus atom, particularly a phosphite, to provide a phosphorus atom with a valence of greater than three, preferably a tetracoordinated phosphorus atom such as, for example, a phosphorothioate, or an equivalent thereof. Suitable sulfurizing agents include, for example, 3H-1,2-benzodithiol-3-one-1,1-dioxide ("Beaucage Reagent"), phenylacetyl disulfide, bis(O,O-diisopropoxyphosphinothioyl) disulfide, and the like.

Selenizing agents that can be used in accordance with the present invention include any suitable reagent that can selenize a tricoordinated phosphorus atom, particularly a phosphite, to provide a phosphorus atom having a valence of greater than three, preferably a tetracoordinated phosphorus atom such as a phosphoroselenoate, or an equivalent thereof. Suitable selenizing agents include, for example, potassium selenocyanate (KSeCN), elemental selenium and the like.

EXAMPLES

The following examples further illustrate the invention but, of course, should not be construed as in any way limiting its scope.

Example 1

This example demonstrates the preparation of 2-[N-Methyl-N-(2-pyridyl)]aminoethanol.

2-Bromopyridine (7.6 mL, 80 mmol) and 2-methylaminoethanol (12.8 mL, 160 mmol) were heated for 24 h in an oil bath kept at 160° C. The reaction mixture was then allowed to cool to ambient temperature and chloroform (300 mL) was added. The solution was shaken with a saturated solution of potassium carbonate (200 mL). The organic layer was dried over anhydrous magnesium sulfate and evaporated to dryness. The material left was distilled under reduced pressure affording a liquid (bp 112-115° C. @ 0.8 torr) (6.4 g, 46 mmol, 58%). 1H NMR (300 MHz, DMSO-d6): δ 8.04 (ddd, J=1.0, 2.0, 4.9 Hz, 1H), 7.46 (ddd J=2.0, 7.0, 8.7 Hz, 1H), 6.58 (ddd J=1.0, 2.0, 8.7 Hz, 1H), 6.51 (ddd J=2.0,4.9, 7.0 Hz, 1H), 3.56 (t, J=1.9 Hz, 4H), 3.01 (s, 3H). 13C NMR (75 MHz, DMSO-d6): δ 36.7, 51.7, 58.5, 105.5, 110.9, 137.0, 147.3, 158.2. FAB-HRMS: calcd for $C_8H_{13}N_2O$ M+H)+ 153.1028, found 153.1034.

Example 2

This example demonstrates the preparation of (±)-1-Phenyl-2-(2-pyridyl)aminoethanol.

(±)-1-Phenyl-2-(2-pyridyl)aminoethanol was prepared according to the procedure of Gray et al., *J. Am. Chem. Soc.*, 81, 4351-4355 (1959) and was isolated as a solid in 60% yield. 1H NMR (300 MHz, DMSO-d6): δ 7.96 (ddd, J=1.0, 2.0, 5.0 Hz, 1H), 7.35 (m, 6H), 6.52 (ddd, J=1.0, 2.0, 8.5 Hz, 1H), 6.47 (ddd, J=2.0, 5.0, 7.0 Hz, 1H), 5.65 (d, J=4.2 Hz, 1H), 4.75 (m, 1H), 3.51 (ddd, J=4.3, 6.7, 13.4 Hz, 1H), 3.26 (ddd, J=5.1, 7.9, 13.4 Hz, 1H). 13C NMR (75 MHz, DMSO-d6): δ 49.2, 71.5, 108.4, 111.5, 125.9, 126.7, 127.9, 136.5, 144.2, 147.2, 158.8. FAB-HRMS: calcd for $C_{13}H_{15}N_2O$ (M+H)+ 215.1184, found 215.1192.

Example 3

This example demonstrates the preparation of (±)-2-[N-Methyl-N-(2-pyridyl)amino]-1-phenylethanol.

(±)-2-[N-Methyl-N-(2-pyridyl)]amino-1-phenylethanol was prepared in a manner identical to that of 1-phenyl-2-(pyridyl)aminoethanol, and was isolated as an oil in 55% yield. The crude oil was redistilled as recommended in the literature.27 1H NMR (300 MHz, DMSO-d6): δ 8.08 (ddd, J=1.0, 2.0, 5.0 Hz, 1H), 7.47 (ddd, J=2.0, 7.0, 8.8 Hz, 1H), 7.32 (m, 5H), 6.60 (m, 1H), 6.54 (ddd, J=2.0, 5.0, 7.0 Hz, 1H), 4.85 (dd, J=4.8, 7.8 Hz, 1H), 3.62 (ddd, J=4.8, 7.8, 14.1 Hz, 2H), 2.90 (s, 3H). 13C NMR (75 MHz, DMSO-d6): δ 37.5, 58.0, 70.8, 105.6, 111.0, 125.8, 126.8, 127.8, 136.9, 144.1, 147.3, 158.1. FAB-HRMS: calcd for $C_{14}H_{17}N_2O$ (M+H)+ 229.1341, found 229.1346.

Example 4

This example demonstrates the preparation of 5'-hydroxyl-protected deoxyribonucleosides bearing 2-(2-pyridyl)amino-ethoxycarbonyl thermolabile hydroxyl protecting groups, as illustrated in FIG. 1.

Dry 3'-O-acetylthymidine (1, 29.6 mg, 0.10 mmol), 1,1'-carbonyldiimidazole (18 mg, 0.11 mmol) and a stirring bar were placed in a flame-dried 4 mL glass vial, which was immediately stoppered with a rubber septum. Anhydrous acetonitrile (0.5 mL) was then added by syringe through the septum, and the reaction mixture was allowed to stir at ambient temperature. (See FIG. 1). A solution of dried in dry acetonitrile was then slowly added by syringe to the magnetically stirred suspension of 1. Thin-layer chromatography (TLC) analysis of the reaction indicated near complete conversion of 1 to the corresponding 5'-O-carbonylimidazolide 2 within 2 h. Then, the selected primary alcohol (i.e., 2-(2-pyridyl)aminoethanol or 2-[N-methyl-N-(2-pyridyl)]amino-ethanol; 0.15 mmol) was added to the reaction mixture followed by 1,1,3,3-tetramethylguanidine (70 μL, 0.55 mmol). The solution was stirred at room temperature until the 5'-O-carbonylimidazolide 2 was completely consumed (~2 h) and a new product was formed as evidenced by TLC. The reaction mixture was then applied onto one preparative TLC plate, which was developed once using dichloromethane/methanol (9:1 v/v) as the mobile phase. The desired UV-absorbing band was cut out and the product was eluted from silica gel using dichloromethane/methanol (9:1 v/v). The solvent was removed by evaporation under reduced pressure affording the 3'-O-acetylthymidine 5'-O-carbonates 3 and 4 in yields ranging from 70-83%. 5'-O-[2-N-(2-Pyridyl)]aminoethyloxycarbonyl-3'-O-acetylthymidine (3). 1H NMR (300 MHz, DMSO-d6): δ 7.94 (m, 1H), 7.46 (m, 1H), 7.34 (ddd, J=2.0, 7.2, 8.4 Hz, 1H), 6.47 (m, 2H), 6.17 (dd, J=6.2, 8.1 Hz, 1H), 5.19 (ddd, J=2.9, 6.8, Hz, 1H), 4.32 (m, 2H), 4.20 (m, 2H), 4.16 (m, 1H), 3.50 (m, 2H), 2.37 (ddd, J=6.8, 8.1, 14.4 Hz, 1H), 2.26 (ddd, J=2.9, 6.2, 14.4 Hz, 1H), 2.05 (s, 3H), 1.76 (d, J=1.0 Hz, 3H). 13C NMR (75 MHz, DMSO-d6): δ11.7, 20.5, 35.4, 66.6, 66.9, 73.5, 80.7, 84.0, 108.2, 109.8, 111.7, 135.5, 136.4, 147.2, 150.1, 154.1, 158.2, 158.3, 163.3, 169.8. FAB-HRMS: calcd for $C_{20}H_{25}N_4O_8$ (M+H)+ 449.1672, found 449.1662. 5'-O-[2-N-Methyl-N-(2-pyridyl)]aminoethyloxycarbonyl-3'-O-acetylthymidine (4). 1H NMR (300 MHz, DMSO-d6): δ 8.04 (ddd, J=1.0, 2.0, 4.9 Hz, 1H), 7.48 (ddd, J=2.0, 7.1, 8.6 Hz, 1H), 7.41 (m, 1H), 6.61 (ddd, J=1.0, 2.0, 8.6 Hz, 1H), 6.55 (ddd, J=2.0, 4.9, 7.1 Hz, 1H), 6.19 (dd, J=8.4 Hz, 1H), 5.15 (ddd, J=2.7, 6.5, 9.3 Hz, 1H), 4.28 (m, 3H), 4.12 (ddd, J=4.8, 7.6, 9.3 Hz, 1H), 3.81 (m, 3H), 2.99 (s, 3H), 2.32 (ddd, J=6.5, 8.4, 14.4 Hz, 1H), 2.22 (ddd, J=2.7, 6.1, 14.4 Hz, 1H), 2.06 (s, 3H), 1.74 (d, J=1.1 Hz, 3H). 13C NMR (75 MHz, DMSO-d6): δ 12.5, 20.6, 35.3, 36.5, 47.6, 49.4, 49.8, 65.6, 67.1, 83.9, 105.5, 109.8, 111.5, 137.2, 137.8, 144.4, 147.3, 154.1, 154.6, 157.9, 169.9. FAB-HRMS: calcd for $C_{21}H_{27}N_4O_8$ (M+H)+ 463.1829, found 463.1855.

Example 5

Figure 2:
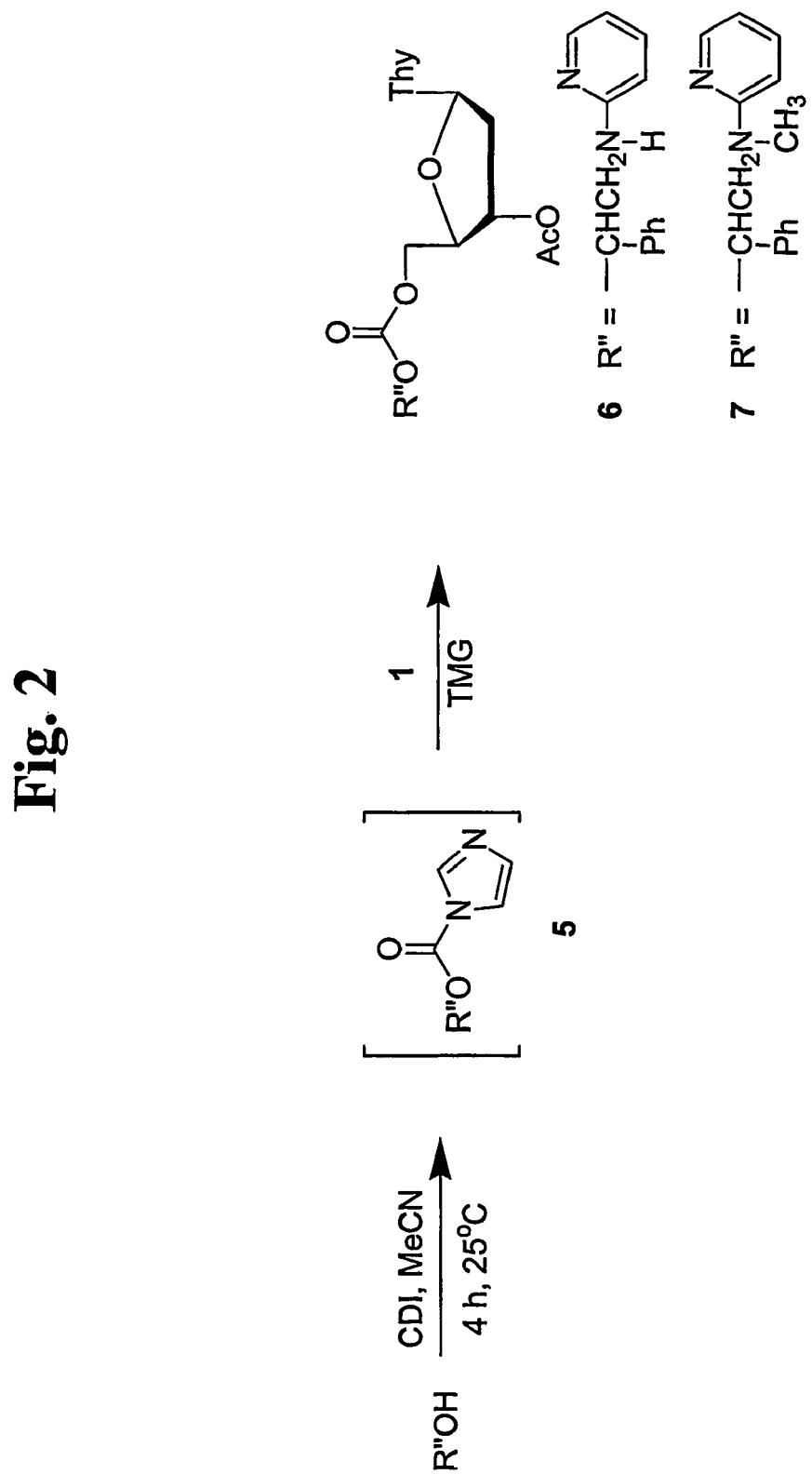
FIG. 2 illustrates the synthesis of a nucleoside in which the 5'-hydroxyl is protected with an exemplary thermolabile hydroxyl-protecting group.

This example demonstrates the preparation of 5'-hydroxyl-protected deoxyribonucleosides bearing 2-(2-pyridyl)amino-ethoxycarbonyl thermolabile hydroxyl protecting groups, as illustrated in FIG. 2.

A dry secondary alcohol, 1-phenyl-2-(2-pyridyl)aminoethanol or 2-[N-methyl-N-(2-pyridyl)]amino-1-phenylethanol, (0.10 mmol), dry 1,1'-carbonyldiimidazole (18 mg, 0.11 mmol) and a stirring bar were placed in a flame-dried 4 mL glass vial, which was immediately stoppered with a rubber septum. Anhydrous acetonitrile (0.5 mL) was then added by syringe through the septum, and the resulting solution was allowed to stir at ambient temperature. Thin-layer chromatography (TLC) analysis of the reaction indicated near complete conversion of the starting alcohol to the corresponding carbonylimidazolide 5 within 4 h. 3'-O-Acetylthymidine (1, 29.6 mg, 0.10 mmol) was then added to the reaction mixture followed by 1,1,3,3-tetramethylguanidine (70 μL, 55 mmol). The solution was stirred at room temperature until the carbonylimidazolide 5 was completely consumed (~2 h) and a new product was formed as evidenced by TLC. The reaction mixture was then applied onto one preparative TLC plate, which was developed once using dichloromethane/methanol (9:1 v/v) as the mobile phase. The desired UV-absorbing band was cut out and the product was eluted from silica gel using dichloromethane/methanol (9:1 v/v). The solvent was removed by evaporation under reduced pressure affording the 5'-hydroxyl-protected deoxyribonucleosides 6 and 7 in yields ranging from 45-73%. 5'-O-[2-(2-pyridyl)]amino-1-phenyl-ethyloxycarbonyl-3'-O-acetylthymidine (6). 1H NMR (300 MHz, CD3CN): δ 8.04 (ddd, J=1.0, 2.0, 5.0 Hz, 1H), 7.40 (m, 6H), 7.33 (q, J=1.4 Hz, 1H), 6.55 (ddd, J=2.0, 5.0, 7.0 Hz, 1H), 6.47 (ddd, J=1.0, 2.0, 8.4 Hz, 1H), 6.13 (dd, J=6.9, 7.2 Hz, 1H), 5.80 (dd, J=4.3, 8.2 Hz, 1H), 5.23 (m, 1H), 4.32 (ddd, J=3.3, 4.6, 12.0 Hz, 2H), 4.17 (ddd, J=3.3, 4.6, 8.0 Hz, 1H), 3.75 (ddd, J=4.3, 8.2, 14.3 Hz, 1H), 3.65 (ddd, J=4.3, 8.2, 14.3 Hz, 1H), 2.32 (m, 2H), 2.04 (s, 3H), 1.78 (d, J=1.4 Hz, 3H). 13C NMR (75 MHz, CD3CN): δ 12.5, 21.1, 37.2, 47.1, 67.9, 74.7, 79.9, 82.6, 86.2, 108.9, 111.6, 113.7, 127.3, 129.4, 129.5, 136.8, 138.1, 139.2, 148.6, 151.5, 155.2, 159.5, 164.5, 171.3. FAB-HRMS: calcd for $C_{26}H_{29}N_4O_8$ (M+H)+ 525.1985, found 525.1998.

Example 6

Figure 3:
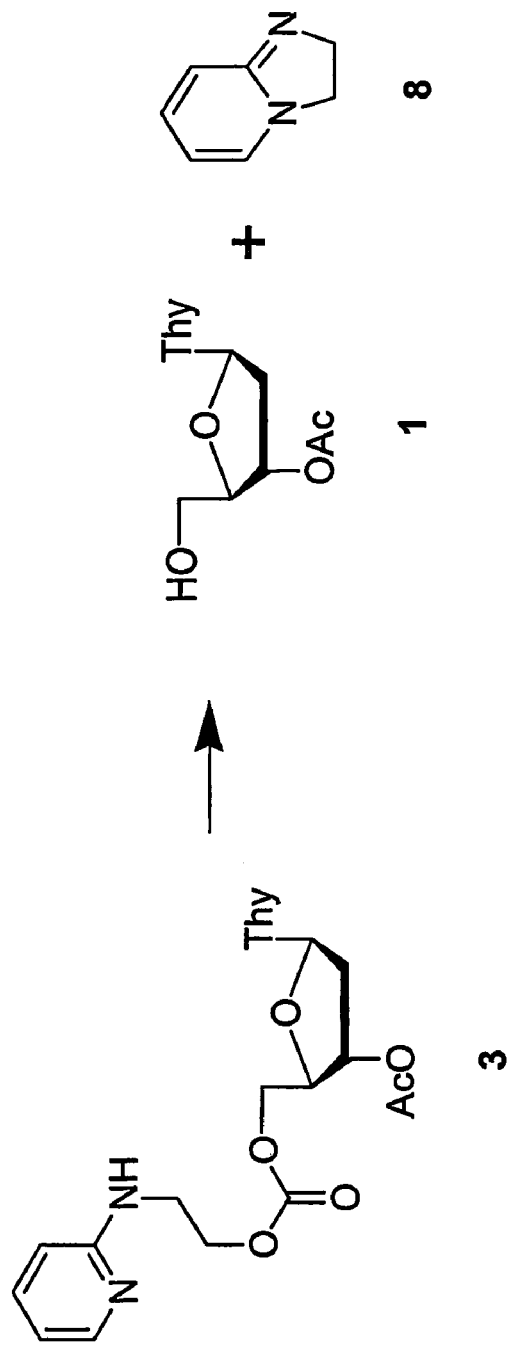
FIG. 3 illustrates the thermal deprotection of a nucleoside protected with an exemplary thermolabile hydroxyl-protecting group.
Figure 4:
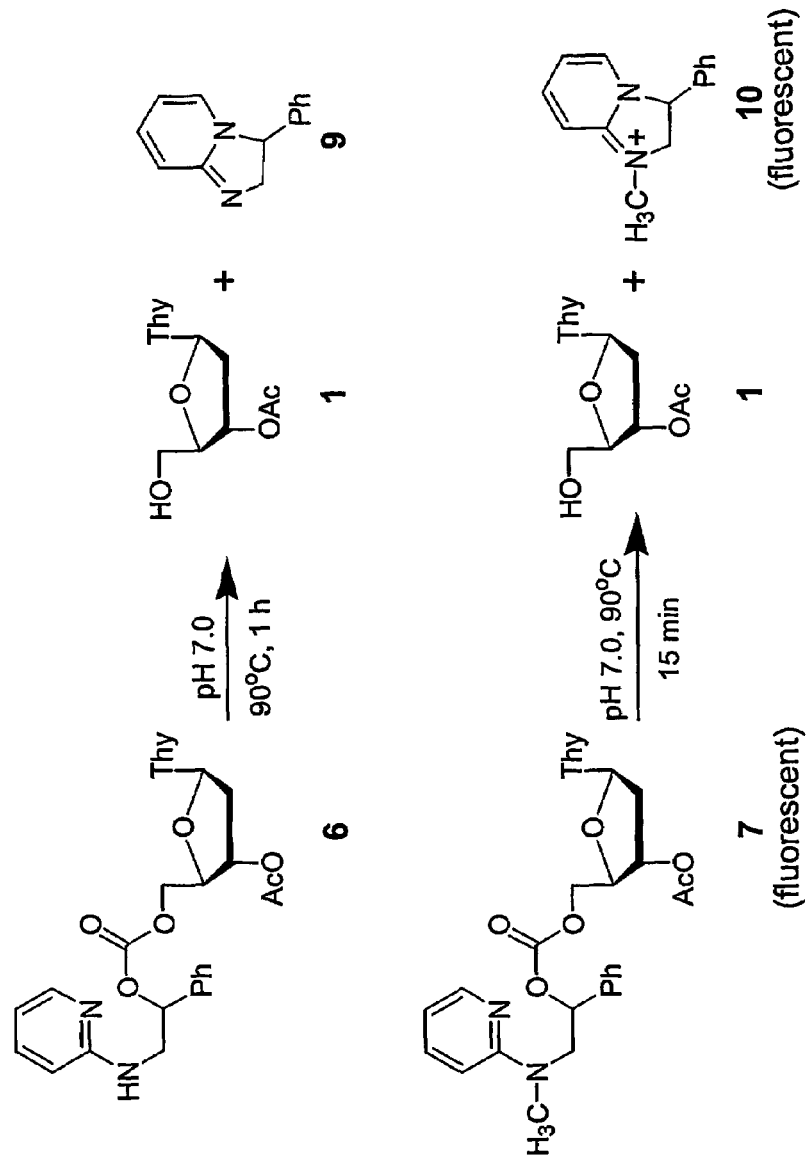
FIG. 4 illustrates the thermal deprotection of a nucleoside protected with an exemplary thermolabile hydroxyl-protecting group.

This example demonstrates the thermolytic deprotection of 5'-hydroxyl-protected deoxyribonucleosides bearing 2-(2-pyridyl)aminoethoxycarbonyl protecting groups, as illustrated in FIGS. 3 and 4.

Samples of 5'-hydroxyl-protected deoxyribonucleosides 3, 4, 6, and 7 individually (~2 mg each) were placed in a 4 mL screw-cap glass vials and dissolved in 0.5 mL MeCN:phosphate buffer (pH 7.0, 3:1 v/v) or EtOH:phosphate buffer (pH 7.0, 1:1 v/v). The solutions were heated to 90±2° C. in a tightly stoppered vial using a heating block. The progress of the thermolytic deprotection reaction was analyzed by reversed-phase high performance liquid chromatograph (RP-HPLC) using a 5 μm Supelcosil™ LC-18S column (25 cm×4.6 mm) and a linear gradient of 1% MeCN/min, starting from 0.1 M triethylammonium acetate pH 7.0, at a flow rate of 1 mL/min.

The time of thermolysis and area % of recovered 5'-hydroxyl-protected deoxyribonucleoside (QOPg), deprotected deoxyribonucleoside 1 (QOH), and thymidine, respectively, are shown in Table 1.

TABLE 1

| QOPg | Time (min) | Area % QOPg | Area % QOH (1) | Area % Thymidine |
|---|---|---|---|---|
| 3 | 120 | 0.4 | 92.6 | 7.0 |
| 4 | 30 | 0.3 | 92.9 | 6.8 |
| 6 | 60 | 0.3 | 92.5 | 7.2 |
| 7 | 15 | 0.2 | 98.8 | 0.9 |

The data shown in Table 1 demonstrate that thermolysis of the 5'-hydroxyl-protected deoxyribonucleosides 3 and 4 primarily resulted in the formation of the deprotected deoxyribonucleoside 1 (see FIG. 3). RP-HPLC analysis of the thermolytic deprotection reaction revealed a peak corresponding to cyclodecarbonation side-product 8 on the basis of $^1$H NMR and mass spectral data. Similarly, thermolytic deprotection of 5'-hydroxyl-protected deoxyribonucleosides 6 and 7 primarily resulted in the formation of deprotected deoxyribonucleoside 1, and cyclodecarbonation side-products 9 and 10, respectively (see FIG. 4). A small amount of 3'-O-deacylation was detected in these experiments, as evidenced by the presence of thymidine.

Example 7

This example demonstrates the thermolytic deprotection of a 5'-hydroxyl-protected deoxyribonucleoside in various solvents.

Thermolytic deprotection of 5'-hydroxyl-protected deoxyribonucleoside 7 was investigated in various solvents including $CCl_4$, dioxane, MeCN, t-BuOH, phosphate buffered EtOH, and phosphate buffered MeCN. Each sample contained 2 mg of the 5'-hydroxyl-protected deoxyribonucleoside 7 and 0.5 mL solvent. The solutions were heated to 90±2° C. for 20 min or as indicated. The products of thermolysis were determined by RP-HPLC analysis using a 5 μm Supelcosil™ LC-18S column (25 cm ☐4.6 mm) and a linear gradient of 1% MeCN/min, starting from 0.1 M triethylammonium acetate, pH 7.0, at a flow rate of 1 mL/min.

The area % of recovered 5'-hydroxyl-protected deoxyribonucleoside QOPg (7), deprotected deoxyribonucleoside QOH (1), and thymidine are presented in Table 2 (ND=not detected).

TABLE 2

| Solvent | Area % QOPg (7) | Area % QOH (1) | Area % Thymidine |
|---|---|---|---|
| $CCl_4$ | 65.6 | 34.4 | ND |
| Dioxane | 56.5 | 43.5 | ND |
| MeCN | 10.0 | 90.0 | ND |
| t-BuOH | 7.1 | 92.9 | ND |
| 1:1 v/v EtOH:phosphate buffer, pH 7; 10 min | ND | 89.6 | 10.4 |
| 3:1 v/v MeCN:phosphate buffer, pH 7 | ND | 98.6 | 1.4 |

The results shown in Table 2 illustrate the effect of solvent on the rate of thermolytic 5'-hydroxyl group deprotection. The fastest rates of 5'-hydroxyl group deprotection were observed in phosphate-buffered EtOH and phosphate-buffered MeCN.

Example 8

This example demonstrates the thermolytic deprotection of 5'-hydroxyl-protected deoxyribonucleosides with a 2-(2-pyridyl)aminoethoxycarbonyl protecting group.

A series of 5'-hydroxyl-protected deoxyribonucleosides of the formula:

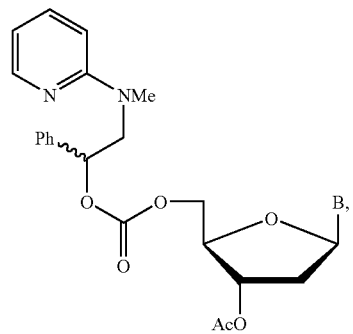

wherein B is 4-N-benzoylcytosin-1-yl (11), 6-N-benzoyladenin-9-yl (12), and 2-N-isobutyrylguanin-9-yl (13) were prepared according to the method described in Example 5. The thermal deprotection of 11-13 was studied following the conditions set forth in Example 3. Specifically, 2 mg of each of the 5'-hydroxyl-protected deoxyribonucleosides 11-13 was dissolved in 0.5 mL of buffer A (1:1 v/v EtOH:phosphate buffer, pH 7.0) or buffer B (3:1 v/v MeCN:phosphate buffer, pH 7.0) and heated at 90±2° C. The time of thermolysis and area % for recovered 5'-hydroxyl-protected deoxyribonucleoside (QOPg) and 5'-O-deprotected-3'-O-acetyl-N-protected deoxyribonucleoside (QOH) are shown in Table 3 (ND=not detected).

TABLE 3

| RO-Pg | Buffer | Time (min) | Area % Recovered QOPg | Area % QOH |
|---|---|---|---|---|
| 11 | A | 5 | 2.1 | 95.3 |
|  | A | 10 | ND | 95.2 |
|  | B | 15 | 0.8 | 97.3 |
|  | B | 20 | ND | 97.3 |

TABLE 3-continued

| RO-Pg | Buffer | Time (min) | Area % Recovered QOPg | Area % QOH |
|---|---|---|---|---|
| 12 | A | 5 | 3.7 | 93.3 |
|  | A | 10 | ND | 92.5 |
|  | B | 15 | 0.2 | 99.1 |
|  | B | 20 | ND | 99.4 |
| 13 | A | 5 | 2.7 | 95.2 |
|  | A | 10 | ND | 95.1 |
|  | B | 15 | 0.3 | 98.1 |
|  | B | 20 | ND | 97.6 |

As illustrated by the data in Table 3, the removal of the 5'-O-protecting group from 11-13 was generally completed within 20 min in phosphate buffered-MeCN and within 10 min in phosphate buffered-EtOH. A small amount of 3'-O-deacylation was detected in these experiments. A more extensive 3'-O-deacylation is obtained in phosphate buffered-EtOH, presumably due to transesterification at elevated temperature. Thermolytic deprotection of 11 led to the production of small amounts of 6-N-benzoyladenine ($\leq$0.1%) and loss of $N^6$-benzoyl protection ($\leq$0.1%) when phosphate buffered-EtOH was used as the solvent.

Example 9

This example demonstrates the synthesis of 2-chloropyridine-N-oxide and 2-chloro-4-nitropyridine-N-oxide.

2-Chloropyridine-N-oxide and 2-chloro-4-nitropyridine-N-oxide were prepared from commercial 2-chloropyridine according to Finger et al, *J. Am. Chem Soc.*, 81, 2674-2675 (1959).

Example 10

This example demonstrates the synthesis of 2-[N-methyl-N-(1-hydroxy-1-phenylethyl)]amino4-nitropyridine-N-oxide (14).

This procedure is an adaptation of the procedure described by Weiner et al., *J. Org. Chem.*, 14, 868-872 (1949). 2-Chloro-4-itropyridine-N-oxide (303 mg, 1.5 mmol) and commercial N-methyl-1-phenyl aminoethanol (339 mg, 2.25 mmol) were dissolved in THF. The solution was heated for 3 days at 55° C. The reaction mixture was then cooled and the formation of a dark yellow precipitate was observed. The precipitate was collected by filtration and dried under vacuum. 2-[N-methyl-N-(1-hydroxy-1-phenylethyl)]amino-4-nitropyridine-N-oxide (14): $^1$H- and $^{13}$C-NMR spectral data were consistent with the structure proposed for 14. ES-MS: calcd for $C_{14}H_{16}N_3O_4$ (M+H)$^+$ 290, found 290.

Example 11

This example demonstrates the preparation of 5'-O-1-phenyl-2-[2-(4-nitropyridinyl-N-oxide)]aminoethoxy carbonyl-3'-O-acetylthymidine (16).

Figure 5:
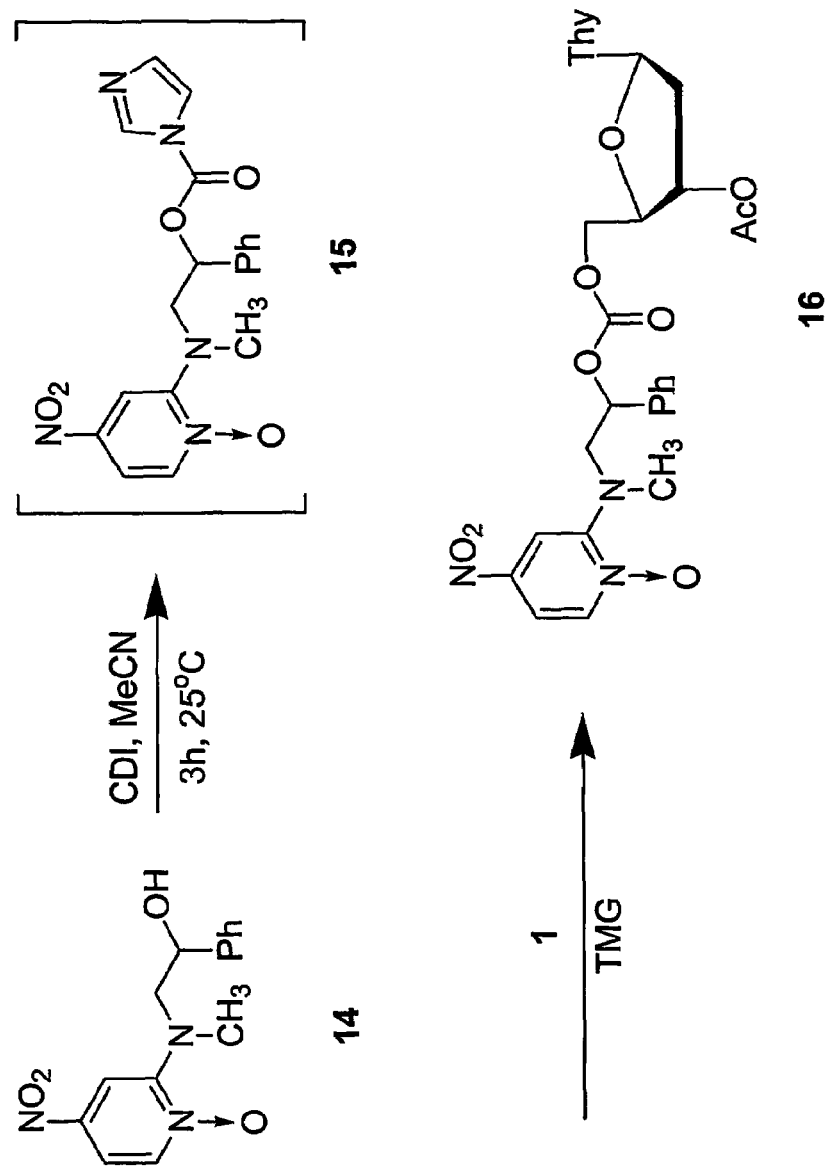
FIG. 5 illustrates the synthesis of a precursor of a nucleoside in which the 5'-hydroxyl is protected with a thermolabile hydroxyl-protecting group.

The 5'-hydroxyl-protected 3'-O-acetylthymidine was prepared according to the method described in Example 2. See FIG. 5. 5'-O-1-phenyl-2-[2-(4-nitropyridinyl-N-oxide)]aminoethoxy carbonyl-3'-O-acetylthymidine (16): $^1$H- and $^{13}$C- NMR spectral data were consistent with the structure proposed for 16. ES-MS: calcd for $C_{27}H_{30}N_5O_{11}$ (M+H)$^+$ 600, found 600.

Example 12

This example demonstrates the thermolytic Deprotection of 5'-O-1-phenyl-2-[2-(4-nitropyridinyl-N-oxide)]aminoethoxy carbonyl-3'-O-acetylthymidine. The 5'-hydroxyl-protected thymidine (2 mg, 3 μmol) was dissolved in acetonitrile (15 μL). To the solution was added TiCl$_3$ (50 mg, 0.3 mmol) in PBS buffer, pH 7.4, (150 μL). See Somei et al., "Titanium (III) chloride for the Reduction of Heteroaromatic and Aromatic Nitro Compounds," *Chem. Pharm. Bull.*, 28, 2515-2518 (1980), for a discussion of titanium-catalyzed reduction reactions. The resulting solution was shaken at ambient temperature for 3 min. Acetonitrile (150 μL) was then added to the reaction mixture and was vigorously shaken. Upon phase separation, the organic phase was collected and co-evaporated with PBS buffer, pH 7.4 (3×150 μL) under reduced pressure. The material left was taken in PBS buffer, pH 7.4, (300 μL) and heated at 90° C. for 5 min.

Figure 6:
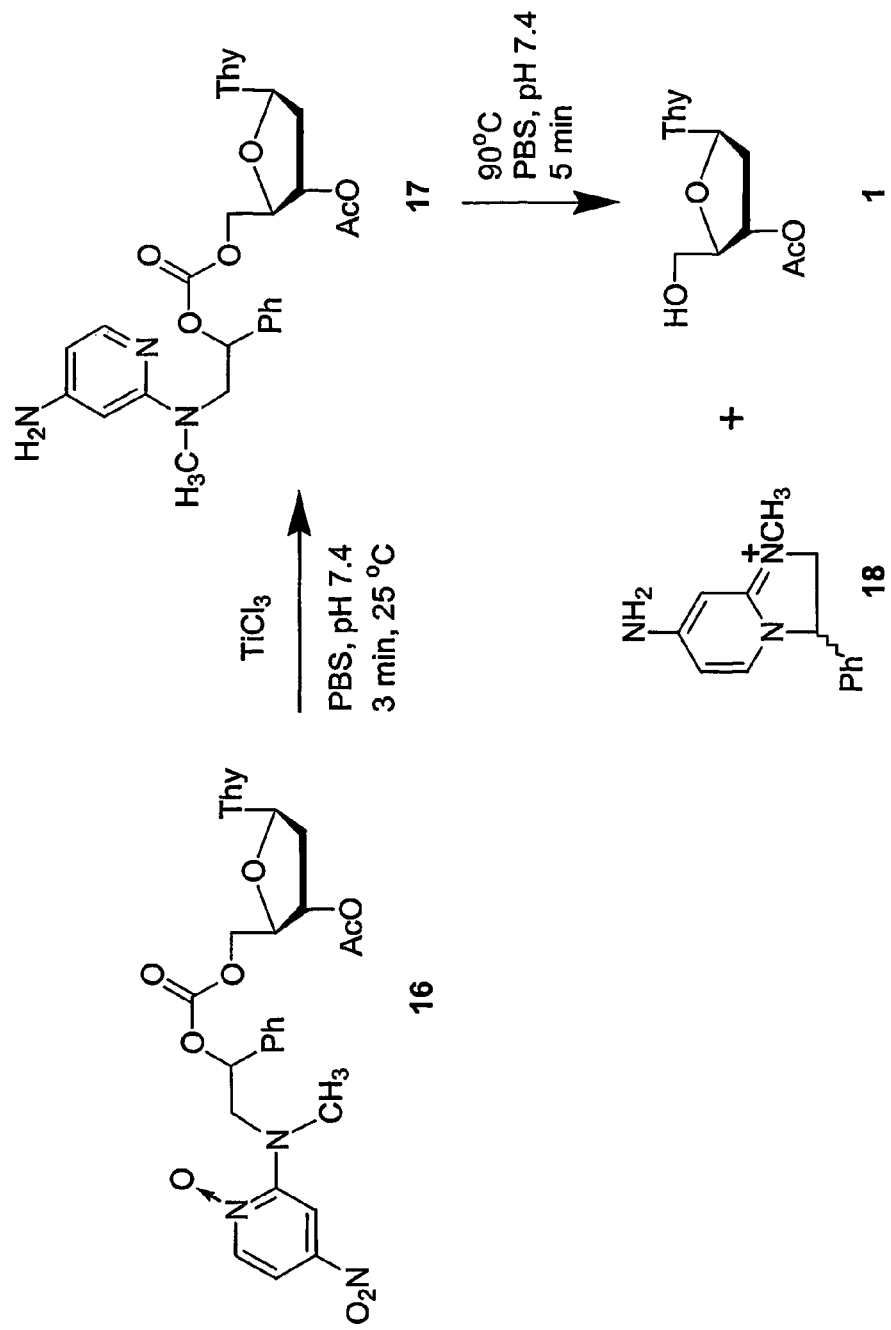
FIG. 6 illustrates the reduction of a thermolabile hydroxyl-protecting group precursor to produce a nucleoside in which the 5'-hydroxyl is protected with a thermolabile hydroxyl-protecting group.
Figure 7:
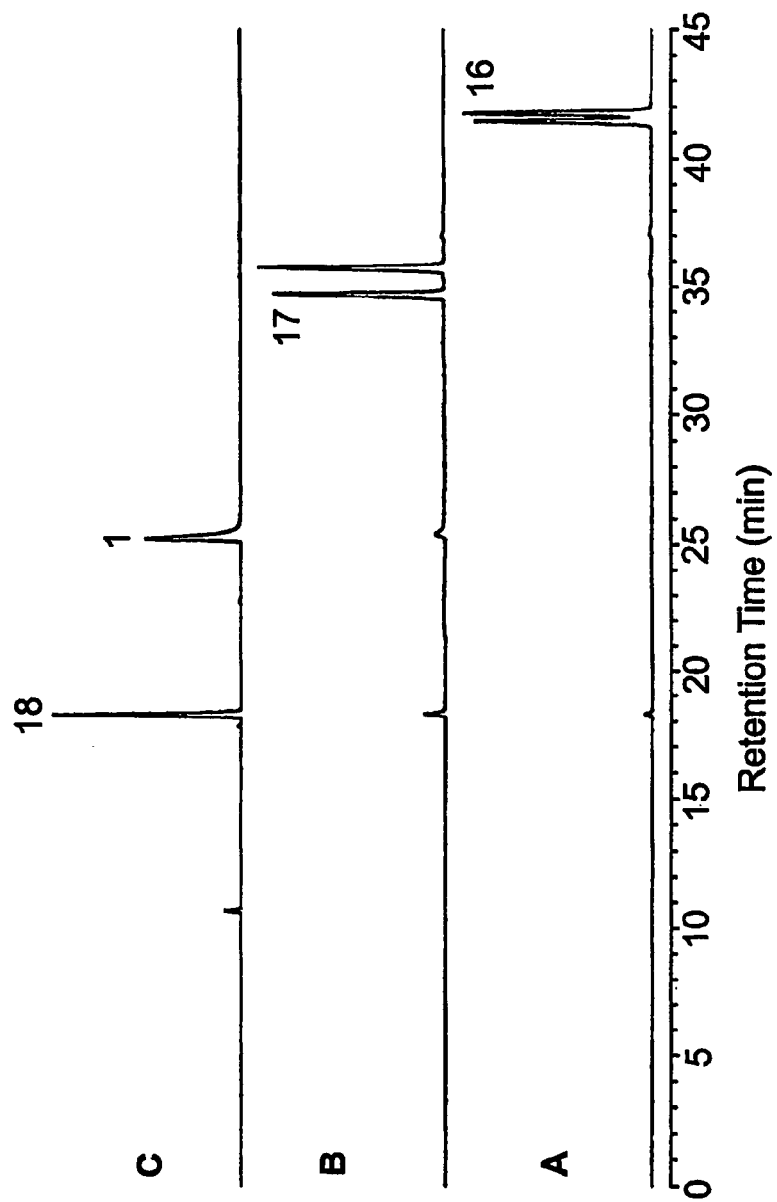
FIG. 7 illustrates RP-HPLC chromatograms of a precursor of a 5'-hydroxyl-protected nucleoside comprising a thermolabile precursor (A), the reduction product thereof (B), and a thermolysis product (C).

The thermolysis reaction is illustrated in FIG. 6. The thermolysis reaction mixture was analyzed by RP-HPLC. Chromatographs depicting the peaks for 5'-O-1-phenyl-2-[2-(4-nitropyridinyl-N-oxide)]aminoethoxy carbonyl-3'-O-acetylthymidine (A), the reduction product (B), and the thermolysis product (C) are shown in FIG. 7.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A hydroxyl-protected alcohol of the formula Pg-O—R, wherein Pg is a protecting group of the formula:

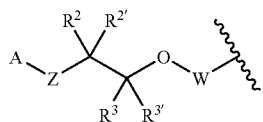
(I)

wherein:

A is a 2-pyridyl group of the formula:

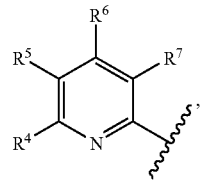

Z is $CH_2$ or $NR^1$;

$R^1$, $R^2$, $R^{2'}$, $R^3$ and $R^{3'}$ are the same or different and each is H, a saturated alkyl, an unsaturated alkyl, an aryl, a saturated alkyl comprising an aryl substituent, or an unsaturated alkyl comprising an aryl substituent, wherein the saturated alkyl, unsaturated alkyl and aryl portions are optionally substituted;

$R^4$, $R^5$, $R^6$, and $R^7$ are the same or different and each is H, an amino, a monoalkylamino, a dialkylamino, a hydroxy, an alkoxy, a halogen, an amide, a saturated alkyl, an unsaturated alkyl, an aryl, a saturated alkyl comprising an aryl, or an unsaturated alkyl comprising an aryl;

W is CO; and

R is a nucleoside, an oligonucleotide, or an oligomer comprising a nucleoside, wherein the protecting group is thermolabile.

2. The hydroxyl-protected alcohol of claim 1, wherein Z is $NR^1$.

3. The hydroxyl-protected alcohol of claim 2, wherein $R^1$ is H or a saturated alkyl.

4. The hydroxyl-protected alcohol of claim 1, wherein, when $R^1$, $R^2$, $R^{2'}$, $R^3$ or $R^{3'}$ is a saturated alkyl, an unsaturated alkyl, a saturated alkyl comprising an aryl substituent, or an unsaturated alkyl comprising an aryl substituent, the unsaturated alkyl or saturated alkyl is unsubstituted or substituted with one or more substituents, which are the same or different, selected from the group consisting of a halogen, a saturated alkyl, an unsaturated alkyl, a hydroxyl, an alkoxy, an aryloxy, an aralkoxy, an ester, an amide, a sulfhydryl, an alkyl sulfide, an aryl sulfide, an alkyl sulfoxide, an aryl sulfoxide, an alkyl sulfonyl, an aryl sulfonyl, a keto, a thioketo, a cyano, and a nitro.

5. The hydroxyl-protected alcohol of claim 1, wherein Pg is selected from the group consisting of:

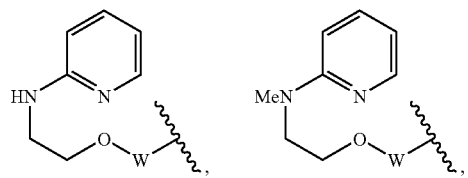

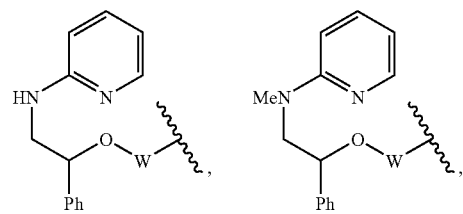

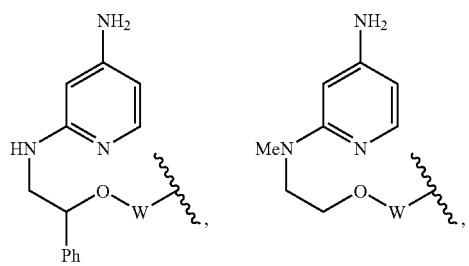

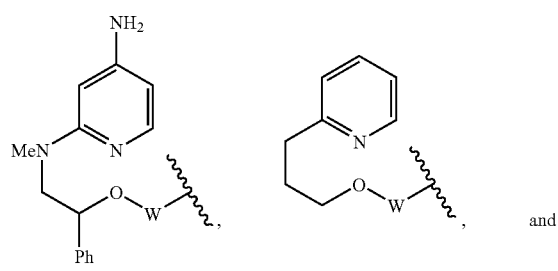

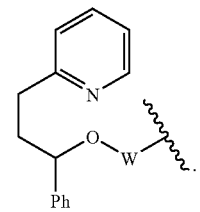

6. A hydroxyl-protected alcohol of the formula Pg-O—R, wherein Pg is a protecting group of the formula:

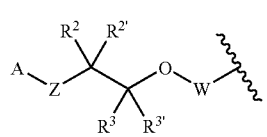
(I)

wherein:

A is a 2-pyridyl group of the formula:

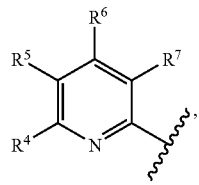

Z is $CH_2$ or $NR^1$;

$R^1$, $R^2$, $R^{2'}$, $R^3$ and $R^{3'}$ are the same or different and each is H, a saturated alkyl, an unsaturated alkyl, an aryl, a saturated alkyl comprising an aryl substituent, or an unsaturated alkyl comprising an aryl substituent, wherein the saturated alkyl, unsaturated alkyl and aryl portions are optionally substituted;

$R^4$, $R^5$, $R^6$, and $R^7$ are the same or different and each is H, an amino, a monoalkylamino, a dialkylamino, a hydroxy, an alkoxy, a halogen, an amide, a saturated alkyl, an unsaturated alkyl, an aryl, a saturated alkyl comprising an aryl, or an unsaturated alkyl comprising an aryl;

W is CO; and

R is the organic residue of the hydroxyl-protected alcohol of the formula:

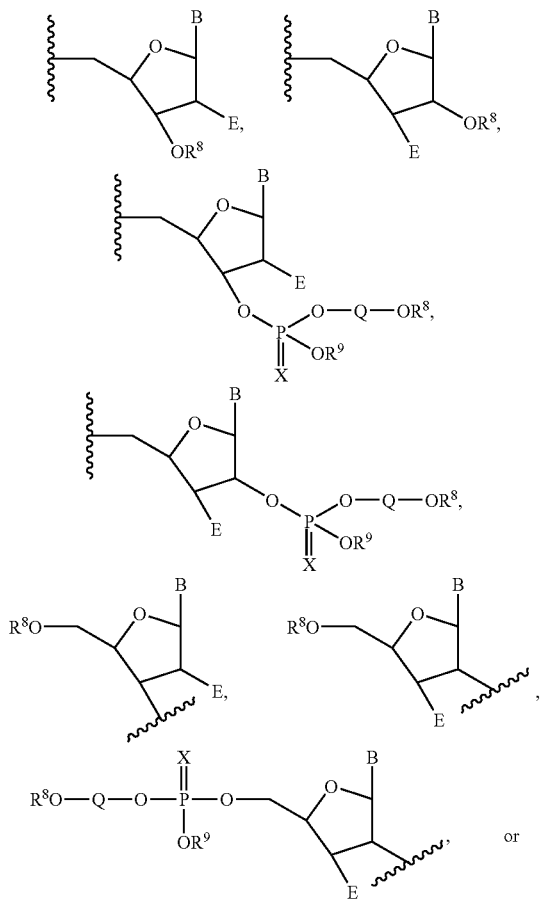

wherein:

Q is a nucleoside, an oligonucleotide, or an oligomer comprising a nucleoside;

X is O, S or Se;

$R^8$ is H, a protecting group or a solid support;

$R^9$ is H or a protecting group;

B is a labeling group, a saturated alkyl, an unsaturated alkyl, a cycloalkyl, an aryl, a heteroaryl comprising from 5 to about 10 atoms in the ring skeleton thereof, a heterocycloalkyl comprising from 3 to about 10 atoms in the ring skeleton thereof, a saturated alkyl comprising an aryl substituent, an unsaturated alkyl comprising an aryl substituent, an amino, an alkylamino, a dialkylamino, a purine, a pyrimidine, adenine, guanine, cytosine, uracil, or thymine, wherein B is unsubstituted or substituted with one or more substituents, which are the same or different, selected from the group consisting of a nucleobase protecting group, $R^{10}$, $OR^{10}$, $NHR^{10}$, $NR^{10}R^{11}$, $N=CH-NR^{10a}R^{11a}$, $N=C(alkyl)-NR^{10a}R^{11a}$, CN, $NO_2$, $N_3$, and a halogen, wherein $R^{10}$ and $R^{11}$ are the same or different and each is H, a saturated alkyl, an unsaturated alkyl, a keto, or a thioketo, and $R^{10a}$ and $R^{11a}$ are the same or different and each is a saturated alkyl or an unsaturated alkyl, or, $R^{10a}$ and $R^{11a}$, together with the nitrogen atom to which they are bonded, form a heterocycle containing 3 to about 7 atoms in the ring skeleton thereof; and E is H, a halogen, $OR^{12}$, $NHR^{12}$, or $NR^{12}R^{13}$, wherein $R^{12}$ and $R^{13}$ are the same or different and each is H, a protecting group, a saturated alkyl, an unsaturated alkyl, a keto or a thioketo;

wherein the protecting group is thermolabile.

7. A method of producing an alcohol, the method comprising heating the hydroxyl-protected alcohol of claim 1, so as to deprotect the hydroxyl-protected alcohol, whereupon an alcohol is produced.

8. The method of claim 7, wherein A is 2-pyridyl or 2-pyridyl having an amino substituent.

9. The method of claim 8, wherein the hydroxyl-protected alcohol is provided by reducing a precursor of the formula:

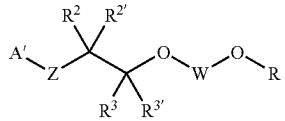

wherein

A' is a 2-pyridyl comprising a nitro-substituent, a 2-pyridyl-1-oxide, or a 2-pyridyl-1-oxide comprising a nitro substituent;

Z is $CH_2$ or $NR^1$, $R^1$, $R^2$, $R^{2'}$, $R^3$ and $R^{3'}$ are the same or different and each is H, a saturated alkyl, an unsaturated alkyl, an aryl, a saturated alkyl comprising an aryl substituent, or an unsaturated alkyl comprising an aryl substituent, wherein the saturated alkyl, unsaturated alkyl and aryl portions are optionally substituted;
W is CO; and
R is the organic residue of the hydroxyl-protected alcohol, so as to produce the hydroxyl-protected alcohol.

10. The method of claim 9, wherein A' is selected from the group consisting of

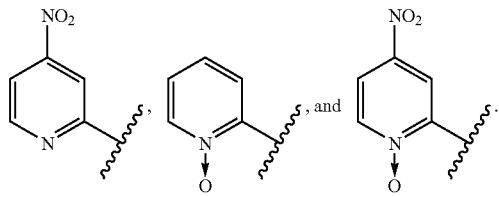

11. The method of claim 9, wherein, when $R^1$, $R^2$, $R^{2'}$, $R^3$ or $R^{3'}$ is a saturated alkyl, an unsaturated alkyl, a saturated alkyl comprising an aryl substituent, or an unsaturated alkyl comprising an aryl substituent, the unsaturated alkyl or saturated alkyl is unsubstituted or substituted with one or more substituents, which are the same or different, selected from the group consisting of a halogen, a saturated alkyl, an unsaturated alkyl, a hydroxy, an alkoxy, an aryloxy, an aralkoxy, an ester, an amide, a sulfhydryl, an alkyl sulfide, an aryl sulfide, an alkyl sulfoxide, an aryl sulfoxide, an alkyl sulfonyl, an aryl sulfonyl, a keto, a thioketo, a cyano, and a nitro.

12. The method of claim 9, wherein the precursor is of the formula:

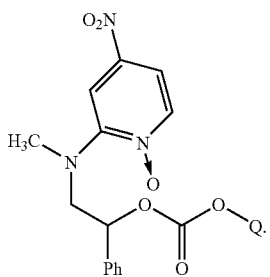

13. The method of claim 7, wherein the hydroxyl-protected alcohol is a 2-(2-pyridyl)aminoethoxycarbonyl protected alcohol.

14. The method of claim 13, wherein the protecting group is selected from the group consisting of:

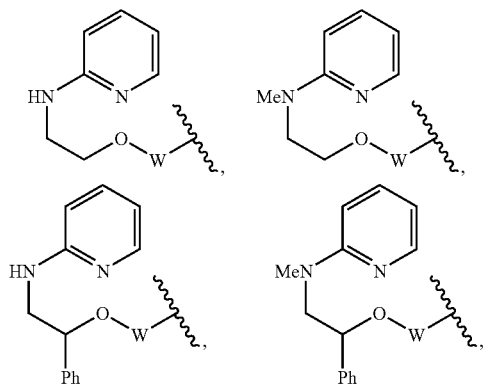

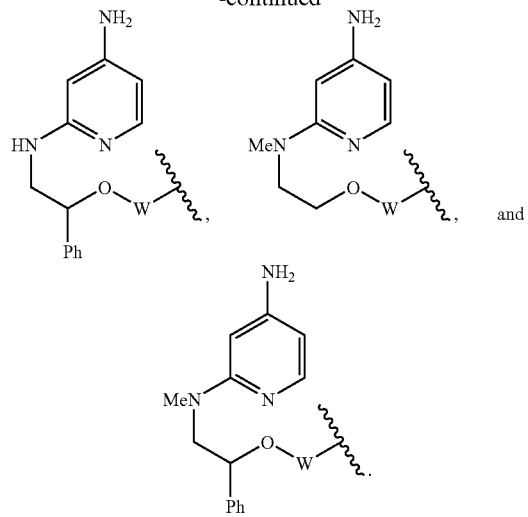

15. A method of producing an oligonucleotide, the method comprising:

(a) reacting a nucleophile with an electrophile to produce an adduct of the formula:

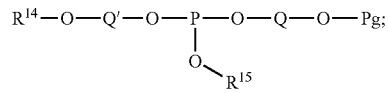

(b) reacting the adduct obtained in step (a) with a reagent selected from the group consisting of oxidizing agents, sulfurizing agents, and selenizing agents to produce a hydroxyl-protected oligonucleotide of the formula:

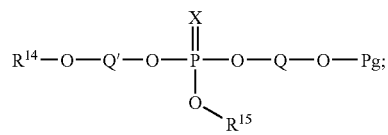

(c) thermally cleaving Pg to produce a nucleophile of the formula;

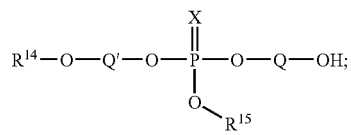

(d) optionally repeating steps (a)-(c) to produce an oligomer of the formula:

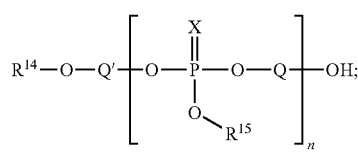

(e) optionally removing $R^{14}$; and
(f) optionally removing $R^{15}$;
wherein:
Pg is a thermolabile hydroxyl-protecting group as defined in claim 1;
n is an integer from 2 to about 300;
$R^{14}$ is a protecting group or a solid support;
$R^{15}$ R is a protecting group;
Q and Q' are the same or different and each is a nucleoside, an oligonucleotide, or an oligomer comprising a nucleoside; and
X is O, S or Se.

16. An alcohol protected with a hydroxyl-protecting group selected from the group consisting of a 2-(2-pyridyl)aminoethoxycarbonyl and a 3-(2-pyridyl) propoxycarbonyl, wherein the alcohol is a nucleoside, an oligonucleotide, or an oligomer comprising a nucleoside.

17. An alcohol protected with a hydroxyl-protecting group selected from the group consisting of a 2-(substituted-2-pyridyl)aminoethoxycarbonyl and a 3-(substituted-2-pyridyl) propoxycarbonyl, wherein the 2-pyridyl ring is substituted with a nitro substituent, a 1-oxide substituent, or a nitro substituent and a 1-oxide substituent.

18. The hydroxyl-protected alcohol of claim 2, wherein $R^1$ is methyl.

19. The hydroxyl-protected alcohol of claim 1, wherein, when $R^1$, $R^2$, $R^{2'}$, $R^3$ or $R^{3'}$ is an aryl, a saturated alkyl comprising an aryl substituent, or an unsaturated alkyl comprising an aryl substituent, the aryl or aryl substituent is unsubstituted or substituted with one or more substituents, which are the same or different, selected from the group consisting of a halogen, a saturated alkyl, an unsaturated alkyl, a hydroxy, an alkoxy, an aryloxy, an aralkoxy, an ester, an amide, a sulfhydryl, an alkyl sulfide, an aryl sulfide, an alkyl sufoxide, an aryl sulfoxide, an alkylsulfonyl, an arylsulfonyl, a keto, a thioketo, a cyano, a nitro, an amino, a monoalkylamino, and a dialkylamino.

20. The hydroxyl-protected alcohol of claim 1, wherein, when $R^1$, $R^2$, $R^{2'}$, $R^3$ or $R^{3'}$ is a saturated alkyl, an unsaturated alkyl, a saturated alkyl comprising an aryl substituent, or an unsaturated alkyl comprising an aryl substituent, the unsaturated alkyl or saturated alkyl is unsubstituted or substituted with one or more substituents, which are the same or different, selected from the group consisting of a halogen, a saturated alkyl, an unsaturated alkyl, a hydroxyl, an alkoxy, an aryloxy, an aralkoxy, an ester, an amide, a sulfhydryl, an alkyl sulfide, an aryl sulfide, an alkyl sulfoxide, an aryl sulfoxide, an alkyl sulfonyl, an aryl sulfonyl, a cyano, and a nitro.

21. The hydroxyl-protected alcohol of claim 1, wherein, when $R^1$, $R^2$, $R^{2'}$, $R^3$ or $R^{3'}$ is an aryl, a saturated alkyl comprising an aryl substituent, or an unsaturated alkyl comprising an aryl substituent, the aryl or aryl substituent is unsubstituted or substituted with one or more substituents, which are the same or different, selected from the group consisting of a halogen, a saturated alkyl, an unsaturated alkyl, a hydroxy, an alkoxy, an aryloxy, an aralkoxy, an ester, an amide, a sulfhydryl, an alkyl sulfide, an aryl sulfide, an alkyl sufoxide, an aryl sulfoxide, an alkylsulfonyl, an arylsulfonyl, a cyano, a nitro, an amino, a monoalkylamino, and a dialkylamino.

22. The hydroxyl-protected alcohol of claim 1, wherein $R^2$ and $R^{2'}$ are H.

23. The hydroxyl-protected alcohol of claim 1, wherein $R^3$ and $R^{3'}$ are H.

24. The hydroxyl-protected alcohol of claim 1, wherein one of $R^3$ and $R^{3'}$ is H and the other is an aryl.

25. The hydroxyl-protected alcohol of claim 1, wherein, when $R^1$, $R^2$, $R^{2'}$, $R^3$ or $R^{3'}$ is an unsaturated alkyl or an unsaturated alkyl comprising an aryl substituent, the unsaturated alkyl is an alkenyl or an alkynyl.

26. A hydroxyl-protected alcohol of the formula Pg-O—R, wherein Pg is a protecting group of the formula:

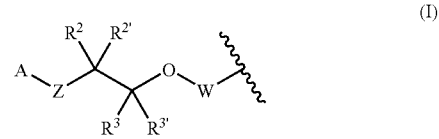

(I)

wherein:
A is a 2-pyridyl group of the formula:

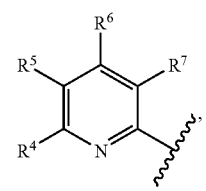

Z is $CH_2$ or $NR^1$;
$R^1$, $R^2$, $R^{2'}$, $R^3$ and $R^{3'}$ are the same or different and each is H, a saturated alkyl, an unsaturated alkyl, an aryl, a saturated alkyl comprising an aryl substituent, or an unsaturated alkyl comprising an aryl substituent, wherein the saturated alkyl, unsaturated alkyl and aryl portions are optionally substituted;
$R^4$, $R^5$, $R^6$, and $R^7$ are the same or different and each is H, an amino, a monoalkylamino, a dialkylamino, a hydroxy, an alkoxy, a halogen, an amide, a saturated alkyl, an unsaturated alkyl, an aryl, a saturated alkyl comprising an aryl, or an unsaturated alkyl comprising an aryl;
W is CO; and
R is the organic residue of the hydroxyl-protected alcohol, wherein when Z is $CH_2$, at least one of $R^2$, $R^{2'}$, $R^3$, $R^{3'}$, $R^4$, $R^5$, $R^6$, and $R^7$ is not H, and
wherein the protecting group is thermolabile.

27. A hydroxyl-protected alcohol of the formula Pg-O—R, wherein Pg is a protecting group of the formula:

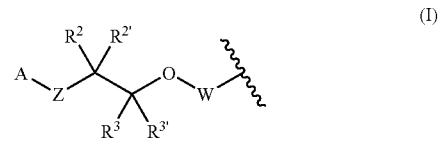

(I)

wherein:
A is a 2-pyridyl group of the formula:

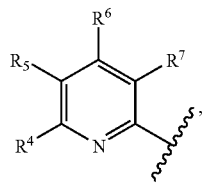

Z is $CH_2$ or $NR^1$;
$R^1$, $R^2$, $R^{2'}$, $R^3$ and $R^{3'}$ are the same or different and each is H, a saturated alkyl, an unsaturated alkyl, an aryl, a saturated alkyl comprising an aryl substituent, or an unsaturated alkyl comprising an aryl substituent, wherein the saturated alkyl, unsaturated alkyl and aryl portions are optionally substituted;
$R^4$, $R^5$, $R^6$, and $R^7$ are the same or different and each is H, an amino, a monoalkylamino, a dialkylamino, a hydroxy, an alkoxy, a halogen, an amide, a saturated alkyl, an unsaturated alkyl, an aryl, a saturated alkyl comprising an aryl, or an unsaturated alkyl comprising an aryl;
W is CO; and
R is the organic residue of the hydroxyl-protected alcohol, wherein R is not a low molecular weight aromatic alcohol, and
wherein the protecting group is thermolabile.

* * * * *

UNITED STATES PATENT AND TRADEMARK OFFICE
CERTIFICATE OF CORRECTION

PATENT NO. : 7,612,197 B2
APPLICATION NO. : 10/556219
DATED : November 3, 2009
INVENTOR(S) : Beaucage et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 738 days.

Signed and Sealed this

Nineteenth Day of October, 2010

David J. Kappos
*Director of the United States Patent and Trademark Office*